(12) United States Patent
Horiba et al.

(10) Patent No.: US 8,264,140 B2
(45) Date of Patent: *Sep. 11, 2012

(54) ORGANIC ELECTROLUMINESCENCE ELEMENT AND DISPLAY DEVICE

(75) Inventors: Koji Horiba, Kanagawa (JP); Hidekazu Hirose, Kanagawa (JP); Tadayoshi Ozaki, Kanagawa (JP); Yohei Nishino, Kanagawa (JP); Mieko Seki, Kanagawa (JP); Takeshi Agata, Kanagawa (JP); Akira Imai, Kanagawa (JP); Katsuhiro Sato, Kanagawa (JP); Kiyokazu Mashimo, Kanagawa (JP); Hirohito Yoneyama, Kanagawa (JP); Toru Ishii, Kanagawa (JP); Daisuke Okuda, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 683 days.

This patent is subject to a terminal disclaimer.

(21) Appl. No.: 12/051,479

(22) Filed: Mar. 19, 2008

(65) Prior Publication Data

US 2009/0039774 A1 Feb. 12, 2009

(30) Foreign Application Priority Data

Aug. 7, 2007 (JP) .................. 2007-205763

(51) Int. Cl.
*H01L 51/54* (2006.01)
*H05B 33/14* (2006.01)
*C09K 11/06* (2006.01)
*C08G 63/66* (2006.01)

(52) U.S. Cl. ... 313/504; 313/506; 257/40; 257/E51.051; 428/690; 528/301

(58) Field of Classification Search ................. None
See application file for complete search history.

(56) References Cited

U.S. PATENT DOCUMENTS 4,092,162 A 5/1978 Wright et al.
(Continued)

FOREIGN PATENT DOCUMENTS

CN 1445258 10/2003
(Continued)

OTHER PUBLICATIONS

Thomas et al., Journal of the American Chemical Society, (2001), vol. 123, pp. 9404-9411.*

(Continued)

*Primary Examiner* — Jennifer Chriss
*Assistant Examiner* — Brett A Crouse
(74) *Attorney, Agent, or Firm* — Fildes & Outland, P.C.

(57) ABSTRACT

An organic electroluminescence element includes a pair of electrodes composed of an anode and a cathode, at least one of which is transparent or semitransparent, and one or more organic compound layers disposed between the pair of electrodes, wherein at least one of the organic compound layers comprises at least one charge-transporting polyester consisting of repeating units containing, as a partial structure, at least one structure represented by the following formula (I-1).

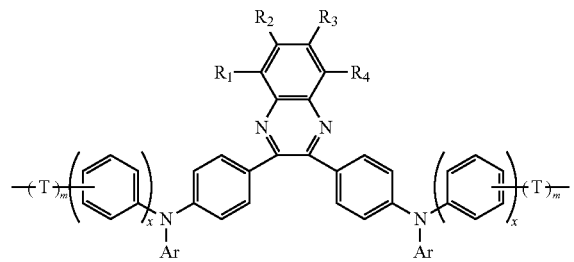

(I-1)

10 Claims, 2 Drawing Sheets

U.S. PATENT DOCUMENTS

| | | | |
|---|---|---|---|
| 4,539,507 A | | 9/1985 | VanSlyke et al. |
| 4,769,292 A * | | 9/1988 | Tang et al. .................... 428/690 |
| 4,801,517 A | | 1/1989 | Frechet et al. |
| 4,806,443 A | | 2/1989 | Yanus et al. |
| 4,806,444 A | | 2/1989 | Yanus et al. |
| 4,937,165 A | | 6/1990 | Ong et al. |
| 4,959,288 A | | 9/1990 | Ong et al. |
| 4,983,482 A | | 1/1991 | Ong et al. |
| 5,034,296 A | | 7/1991 | Ong et al. |
| 5,674,635 A * | | 10/1997 | Hsieh et al. .................... 428/690 |
| 5,879,821 A * | | 3/1999 | Hsieh ............................ 428/690 |
| 6,652,995 B2 * | | 11/2003 | Seki et al. ..................... 428/690 |
| 6,670,052 B2 * | | 12/2003 | Hirose et al. .................. 428/690 |
| 7,166,859 B2 * | | 1/2007 | Hirose et al. .................. 257/40 |
| 2001/0024738 A1 * | | 9/2001 | Hawker et al. ................. 428/690 |
| 2003/0207187 A1 | | 11/2003 | Seki et al. |
| 2004/0018384 A1* | | 1/2004 | Hirose et al. .................. 428/690 |
| 2004/0081854 A1* | | 4/2004 | Hirose et al. .................. 428/690 |
| 2005/0014020 A1* | | 1/2005 | Yoneyama et al. ............ 428/690 |
| 2005/0065342 A1* | | 3/2005 | Shitagaki et al. .............. 544/353 |
| 2005/0186446 A1* | | 8/2005 | Shitagaki et al. .............. 428/690 |
| 2006/0046094 A1* | | 3/2006 | Nishino et al. ................ 428/690 |
| 2006/0267487 A1* | | 11/2006 | Ozaki et al. ................... 313/504 |
| 2007/0059553 A1 | | 3/2007 | Egawa et al. |
| 2007/0148493 A1* | | 6/2007 | Yoneyama et al. ............ 428/690 |
| 2007/0281076 A1* | | 12/2007 | Okuda et al. .................. 427/66 |
| 2008/0306239 A1 | | 12/2008 | Horiba et al. |
| 2008/0311425 A1* | | 12/2008 | Okuda et al. .................. 428/690 |
| 2009/0001876 A1* | | 1/2009 | Okuda et al. .................. 313/504 |

FOREIGN PATENT DOCUMENTS

| | | |
|---|---|---|
| JP | 53-053676 | 5/1978 |
| JP | 59-028903 | 7/1984 |
| JP | 59-194393 | 11/1984 |
| JP | 61-020953 | 1/1986 |
| JP | 01-134456 | 5/1989 |
| JP | 01-134457 | 5/1989 |
| JP | 01-134462 | 5/1989 |
| JP | 04-133065 | 5/1992 |
| JP | 04-133066 | 5/1992 |
| JP | 05-148350 | 6/1993 |
| JP | 10-92576 | 4/1998 |
| JP | 2006-016384 | 1/2006 |
| JP | 2008-303169 | 12/2008 |

OTHER PUBLICATIONS

Thomas et al., Chemistry of Materials, (2002), vol. 14, pp. 2796-2802.*
Horiba, Declaration, U.S. Appl. No. 12/041,277, filed Jul. 22, 2011.*
Thin Solid Films, 94, 1982, pp. 171-183.
Appl. Phys. Lett. vol. 51, Sep. 21, 1987, pp. 913-915.
Technical Report of IEICE, OME95-54, 1995, pp. 47-52.
Proceedings of the 40$^{th}$ Applied Physics Related Associated Seminar, 30a-SZK-14, 1993.
Nature, vol. 357, Jun. 11, 1992, pp. 477-479.
Polymer Preprints, Japan, vol. 42, No. 7, 20J-21, 1993, pp. 2860-2863.
Proceedings of the 38$^{th}$ Applied Physics Related Associated Seminar, 31p-G-12, 1991.
Proceedings of the 50$^{th}$ Applied Physics Society Seminar, 29p-ZP-5, 1989.
Proceedings of the 51$^{th}$ Applied Physics Society Seminar, 28a-PB-7, 1990.
Nov. 17, 2010 Office Action issued in U.S. Appl. No. 12/041,277.
Apr. 22, 2011 Office Action issued in U.S. Appl. No. 12/041,277.

* cited by examiner

ORGANIC ELECTROLUMINESCENCE ELEMENT AND DISPLAY DEVICE

CROSS-REFERENCE TO RELATED APPLICATION

This application is based on and claims priority under 35 USC 119 from Japanese patent Application No. 2007-205763 filed on Aug. 7, 2007.

BACKGROUND OF THE INVENTION

1. Technical Field

The present invention relates to an organic electroluminescence element and a display device.

2. Related Art

Organic electroluminescence elements are promising for a wide range of applications because they are self-luminescent fully solid-state elements with high visibility and resistance to impact. Currently, although those using inorganic fluorescent materials are predominant and widely used, they have problems in that the running cost is high since an alternating voltage of 200 V or more at 50 Hz to 1000 Hz is necessary for operation, and in that the brightness is insufficient. On the other hand, organic electroluminescence element research using organic compounds was initiated by using single crystals of anthracene and the like at first, but the film thickness was as thick as approximately 1 mm, and a driving voltage of 100 V or more was required.

The luminescence of these elements is a phenomenon in which an electron is injected from one electrode and a hole is injected from the other electrode, whereby a fluorescent material in the element is excited to a high energy level, and the excited fluorescent material returns to the ground state through emission of excessive energy as light.

These electroluminescence elements having a layered structure has a structure in which an organic fluorescent material and a charge transporting organic matter (charge transporting material) are layered on an electrode, and holes and electrons are transferred in the charge transporting material and recombine with each other to emit light. Organic fluorescent material to be used include 8-quinolinol aluminum complexes and fluorescence-emitting organic dyes such as coumarin compounds. Examples of the charge transporting material include diamino compounds such as N,N-di(m-tolyl)N,N'-diphenylbenzidine and 1,1-bis[N,N-di(p-tolyl)aminophenyl]cyclohexane, and 4-(N,N-diphenyl)aminobenzaldehyde-N,N-diphenylhydrazone compounds.

SUMMARY

An object of the present invention is to provide an organic electroluminescence element exhibiting high luminescence intensity, high light emitting efficiency and a long lifetime, and being capable of easy manufacturing. Another object of the invention is to provide a display device utilizing the above organic electroluminescence element.

According to an aspect, there is provided an organic electroluminescence element including a pair of electrodes composed of an anode and a cathode, at least one of which is transparent or semitransparent, and one or more organic compound layers disposed between the pair of electrodes, wherein at least one of the organic compound layers includes at least one charge-transporting polyester consisting of repeating units containing, as a partial structure, at least one structure represented by the following formula (I-1):

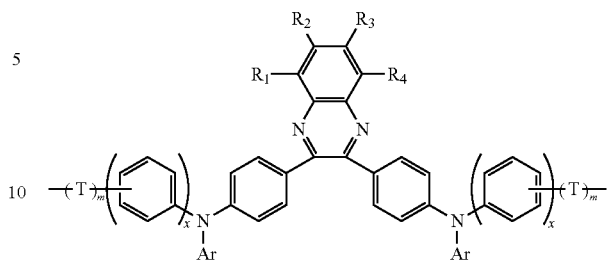

(I-1)

In the formula (I-1), $R_1$, $R_2$, $R_3$ and $R_4$ each independently represent a hydrogen atom, a substituted or unsubstituted monovalent hydrocarbon group having 1 to 10 carbon atoms, a substituted or unsubstituted monovalent phenyl group, a halogen atom, a substituted or unsubstituted monovalent polynuclear aromatic hydrocarbon group having 2 to 10 aromatic rings, a substituted or unsubstituted monovalent condensed aromatic hydrocarbon group having 2 to 10 aromatic rings, or a substituted or unsubstituted monovalent aromatic heterocyclic group; Ar represents a substituted or unsubstituted monovalent phenyl group, a substituted or unsubstituted monovalent polynuclear aromatic hydrocarbon group having 2 to 10 aromatic rings, a substituted or unsubstituted monovalent condensed polycyclic aromatic hydrocarbon group having 2 to 10 aromatic rings, a substituted or unsubstituted monovalent aromatic heterocyclic group, or a monovalent aromatic group containing at least one aromatic heterocycle; x represents an integer of 1 to 3; T represents a divalent linear hydrocarbon group having 1 to 10 carbon atoms or a divalent branched hydrocarbon group having 2 to 10 carbon atoms; and m represents an integer of 0 to 3.

BRIEF DESCRIPTION OF THE DRAWINGS

Exemplary embodiments of the present invention will be described in detail based on the following figures, wherein.

DETAILED DESCRIPTION

Figure 1:
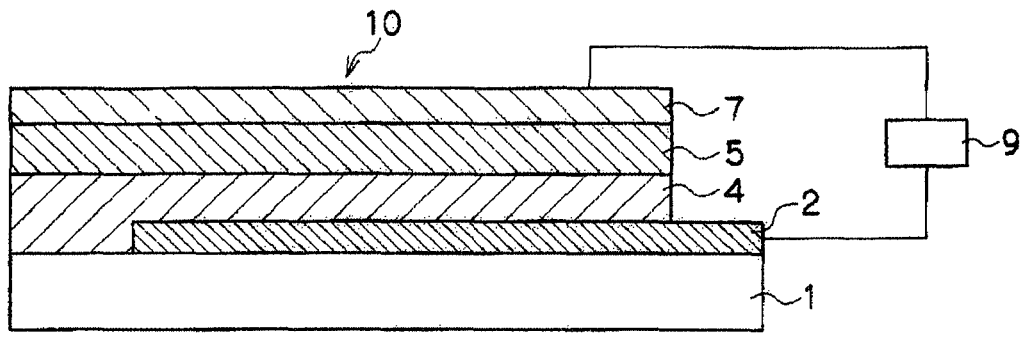
FIG. 1 is a schematic diagram showing a display device in an exemplary embodiment.

Hereinafter, the present invention is described in detail by reference to an exemplary embodiment.

The organic electroluminescence element in the exemplary embodiment is an organic electroluminescence element including a pair of electrodes composed of an anode and a cathode, at least one of which is transparent or semitransparent, and one or plural organic compound layers disposed between the pair of electrodes, wherein at least one of the organic compound layers includes at least one charge-transporting polyester consisting of repeating units containing, as a partial structure, at least one structure selected from the structures represented by the formula (I-1) below (hereinafter simply referred to as "charge transporting polyester" in some cases).

By selecting the structure of the charge-transporting polyester, the charge-transporting polyester may be endowed with either a hole transporting ability or an electron transporting ability. Accordingly, the charge-transporting polyester may be used in any of a hole-transporting layer, a light-emitting layer, an electron-transporting layer etc., depending on the object.

Hereinafter, the exemplary embodiment is described in detail first by reference to the charge-transporting polyester.

The charge-transporting polyester has repeating units containing, as a partial structure, at least one structure selected from the structures represented by the following formula (I-1):

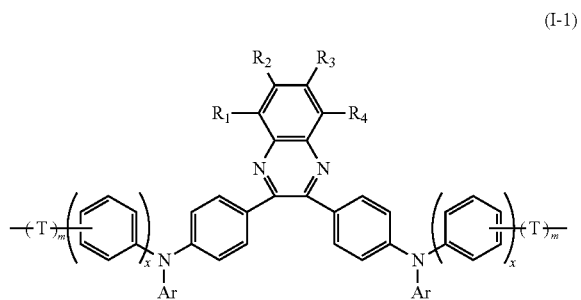

wherein, in the formula (I-1), $R_1$, $R_2$, $R_3$ and $R_4$ each independently represent a hydrogen atom, a substituted or unsubstituted monovalent hydrocarbon group having 1 to 10 carbon atoms, a substituted or unsubstituted monovalent phenyl group, a halogen atom, a substituted or unsubstituted monovalent polynuclear aromatic hydrocarbon group having 2 to 10 aromatic rings, a substituted or unsubstituted monovalent condensed aromatic hydrocarbon group having 2 to 10 aromatic rings, or a substituted or unsubstituted monovalent aromatic heterocyclic group; Ar represents a substituted or unsubstituted monovalent phenyl group, a substituted or unsubstituted monovalent polynuclear aromatic hydrocarbon group having 2 to 10 aromatic rings, a substituted or unsubstituted monovalent condensed polycyclic aromatic hydrocarbon group having 2 to 10 aromatic rings, a substituted or unsubstituted monovalent aromatic heterocyclic group, or a monovalent aromatic group containing at least one aromatic heterocycle; x represents an integer of 1 to 3; T represents a divalent linear hydrocarbon group having 1 to 10 carbon atoms or a divalent branched hydrocarbon group having 2 to 10 carbon atoms; and m represents an integer of 0 to 3.

In the formula (I-1), the hydrocarbon group selected as a structure for $R_1$ to $R_4$ may be linear or branched.

The number of carbon atoms constituting the linear hydrocarbon group is preferably from 1 to 8, more preferably from 1 to 6.

On the other hand, the number of carbon atoms constituting the branched hydrocarbon group is preferably from 3 to 7, more preferably from 3 to 5.

The number of aromatic rings constituting the polynuclear aromatic hydrocarbon group or the condensed aromatic hydrocarbon group selected as a structure for $R_1$ to $R_4$ and Ar in the formula (I-1) may be from 2 to 10, but in the condensed aromatic hydrocarbon group, the number of aromatic rings may be from 1 to 5.

In the present exemplary embodiment, a specific definition for the terms "polynuclear aromatic hydrocarbon", "condensed aromatic hydrocarbon", "aromatic heterocycle", and "aromatic group containing an aromatic heterocycle", are given below.

The "polynuclear aromatic hydrocarbon" is a hydrocarbon containing two or more aromatic rings which consist of carbon and hydrogen atoms and which are bound to each other via a carbon-carbon bond. Specific examples thereof include biphenyl and terphenyl.

The "condensed aromatic hydrocarbon" is a hydrocarbon compound having two or more aromatic rings consisting of carbon and hydrogen atoms wherein there are a pair of vicinal carbon atoms bonded to each other that are shared by aromatic rings. Specific examples thereof include naphthalene, anthracene, pyrene, phenanthrene, perylene, and fluorene.

The "aromatic heterocycle" represents an aromatic ring also containing one or more other elements than carbon and hydrogen. The scope of the aromatic heterocycle encompasses a heterocycles substituted by an aromatic ring and an aromatic ring substituted by a heterocycle. In the heterocycle, the number (Nr) of the atoms constituting the cyclic skeleton thereof may be 5 or 6. The kind and number of other atoms (heteroatoms) than carbon atoms in the cyclic skeleton are not particularly limited. For example, a sulfur atom, a nitrogen atom, an oxygen atom or the like may be used. The cyclic skeleton may contain two kinds of heteroatoms and/or two or more heteroatoms. In particular, thiophene, pyrrole, furan or a heterocycle obtained by substituting the carbon atom at the 3- or 4-position of any of the above compounds with a nitrogen atom may be used as a heterocycle having a 5-memberred ring structure, and pyridine may be used as a heterocycle having a 6-memberred ring structure. The scope of the aromatic ring includes polynuclear aromatic hydrocarbons and condensed aromatic hydrocarbons in addition to a phenyl group.

The "aromatic group containing an aromatic heterocycle" represents a bonding group containing at least one kind of aromatic heterocycle in the atomic group constituting the skeleton.

Such aromatic compounds and groups may have a structure in which the entire structure is conjugated or a part of the structure is conjugated. From the viewpoint of charge-transporting efficiency and light emitting efficiency, those having a structure in in which the entire structure is conjugated are preferred.

Examples of a substituent that can be substituted on a group selected as a structure for each of $R_1$ to $R_4$ and Ar in the formula (I-1) include a hydrogen atom, an alkyl group, an alkoxy group, an aryl group, an aralkyl group, a substituted amino group, and a halogen atom. The alkyl group may be a group having 1 to 10 carbon atoms, such as a methyl group, an ethyl group, a propyl group or an isopropyl group. The alkoxy group may be a group having 1 to 10 carbon atoms, such as a methoxy group, an ethoxy group, a propoxy group or an isopropoxy group. The aryl group may be a group having 6 to 20 carbon atoms, such as a phenyl group or a toluyl group. The aralkyl group may be a group having 7 to 20 carbon atoms, such as a benzyl group or a phenethyl group. Examples of a substituent in the substituted amino group include an alkyl group, an aryl group and an aralkyl group, and specific examples thereof are as described above.

Among these groups, a phenyl group, a biphenyl group, a fluorine atom or a trifluoromethyl group is preferable as a substituent that can be substituted on a group selected as a structure for Ar from the viewpoint of increasing the ionization potential. From the viewpoint of decreasing the ionization potential, a substituted amino group (e.g., a triphenylamino group) or an alkoxy group (e.g., a methoxy group) is preferable as a substituent that can be substituted oil a group selected as a structure for Ar. For further improving the solubility in a solvent and resin and compatibility therewith, an alkyl group such as a methyl group, a hexyl group or an octyl group is preferable as a substituent that can be substituted on a group selected as a structure for each of $R_1$ to $R_4$, and a hexyl group is more preferable.

In the formula (I-1), X represents an integer of 1 to 3, but is preferably 1 to 2 from the viewpoint of solubility in a solvent and resin and compatibility therewith. Particularly, X is preferably 2 for realizing balanced improvement of characteristics including charge injection property, charge mobility, thin film forming ability, emission property, heat stability during light emission, and storage stability.

In the formula (I-1), T represents a divalent linear hydrocarbon group having 1 to 10 carbon atoms or a divalent branched hydrocarbon group having 2 to 10 carbon atoms, and may be selected from a divalent linear hydrocarbon group having 2 to 6 carbon atoms and a divalent branched hydrocarbon group having 3 to 7 carbon atoms. Among these groups, the following divalent hydrocarbon groups are particularly preferable.

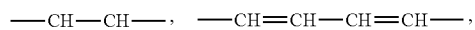
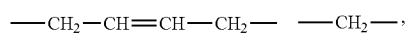
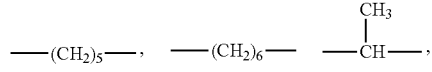
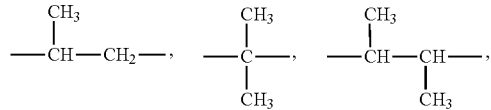
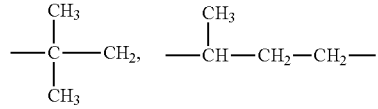
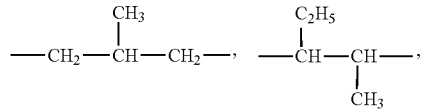
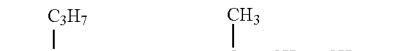
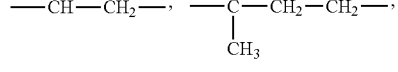

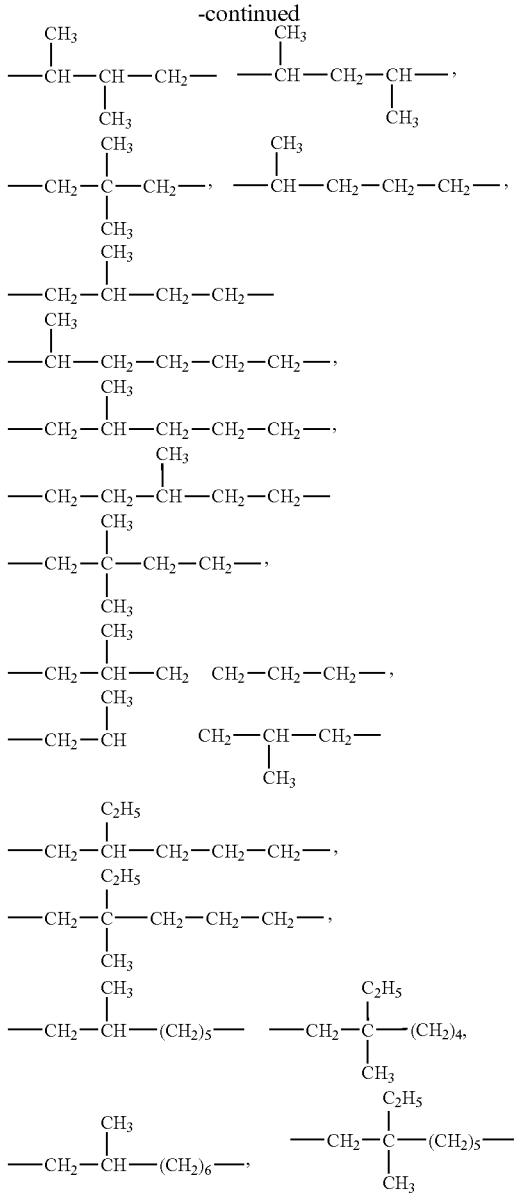

Specific examples of the structures represented by the formula (I-1) above are shown below:

| *St | Ar | $R_1$ | $R_2$ | $R_3$ | $R_4$ | X | m | T | *B.P. |
|---|---|---|---|---|---|---|---|---|---|
| 1 | phenyl | —H | —H | —H | —H | 1 | 1 | —(CH$_2$)$_2$— | 3 |
| 2 | phenyl | —H | —H | —H | —H | 1 | 1 | —(CH$_2$)$_2$— | 4 |
| 3 | phenyl | —H | —CH$_3$ | —H | —H | 1 | 1 | —(CH$_2$)$_2$— | 3 |

-continued
| *St | Ar | R₁ | R₂ | R₃ | R₄ | X | m | T | *B.P. |
|---|---|---|---|---|---|---|---|---|---|
| 4 | 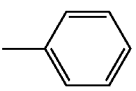 | —H | —CH₃ | —CH₃ | —H | 2 | 1 | —(CH₂)₂— | 4,4' |
| 5 | 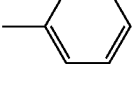 | —H | —F | —H | —H | 1 | 1 | —(CH₂)₂— | 4 |
| 6 | 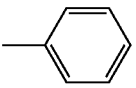 | —H | —CH₂CH₃ | —H | —H | 1 | 1 | —(CH₂)₂— | 4 |
| 7 | 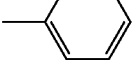 | —H | —CH₃ | —H | —H | 3 | 1 | 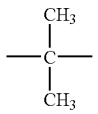 | 4',4'' |
| 8 | 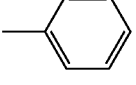 | —CH₃ | —H | —H | —H | 1 | 1 | —(CH₂)₂— | 4 |
| 9 | 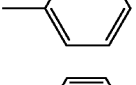 | —H | 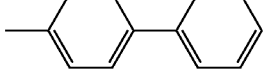 | —H | —H | 1 | 1 | —(CH₂)₂— | 4 |
| 10 | 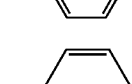 | —H | 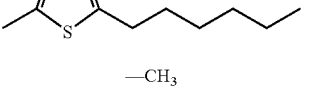 | —H | —H | 1 | 1 | —(CH₂)₂— | 4 |
| 11 | 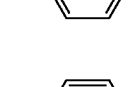 | —CH₃ | —CH₃ | —H | —H | 1 | 1 | 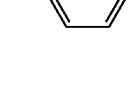 | 4 |
| 12 | 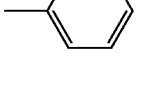 | —H | 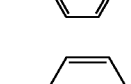 | —H | —H | 1 | 1 | 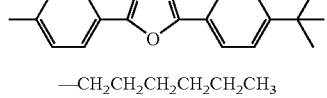 | 4 |
| 13 | 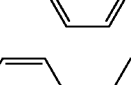 | —H | 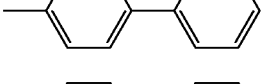 | —H | —H | 1 | 1 | —(CH₂)₂— | 4 |
| 14 | 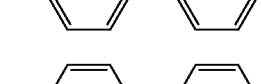 | —H | —CH₂CH₂CH₂CH₂CH₂CH₃ | —H | —H | 2 | 1 | —(CH₂)₂— | 4,4' |
| 15 | 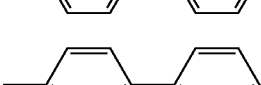 | —H | —H | —H | —H | 1 | 1 | —(CH₂)₂— | 3 |
| 16 | 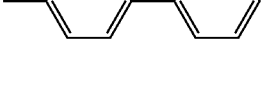 | —H | —H | —H | —H | 1 | 1 | —(CH₂)₂— | 4 |
| 17 |  | —H | —CH₃ | —H | —H | 1 | 1 | —(CH₂)₂— | 4 |
| 18 |  | —H | —CH₃ | —CH₃ | —H | 2 | 1 | —(CH₂)₂— | 4,4' |

-continued

| *St | Ar | R₁ | R₂ | R₃ | R₄ | X | m | T | *B.P. |
|---|---|---|---|---|---|---|---|---|---|
| 19 | biphenyl | —H | —F | —H | —H | 1 | 1 | —(CH$_2$)$_2$— | 4 |
| 20 | biphenyl | —H | —CH$_2$CH$_3$ | —H | —H | 1 | 1 | —(CH$_2$)$_2$— | 4 |
| 21 | phenylpyridine | —CH$_2$CH$_3$ | —H | —H | —H | 2 | 1 | —CH(CH$_3$)—CH$_2$—CH$_2$— | 4,4' |
| 22 | phenylpyridine | —H | 2-thienyl | —H | —H | 1 | 1 | —(CH$_2$)$_2$— | 4 |
| 23 | phenylpyridine | H | 4-biphenyl | —H | —H | 1 | 1 | —(CH$_2$)$_3$— | 4 |
| 24 | biphenyl | —H | 5-hexyl-2-thienyl | —H | —H | 1 | 1 | —(CH$_2$)$_3$— | 4 |
| 25 | biphenyl | —H | phenyl | —H | —H | 1 | 1 | —(CH$_2$)$_2$— | 4 |
| 26 | biphenyl | H | —F | —H | —H | 1 | 1 | —(CH$_2$)$_3$— | 4 |
| 27 | biphenyl | —H | —F | —F | —H | 1 | 1 | —CH(CH$_3$)—CH$_2$—CH$_2$— | 4 |
| 28 | biphenyl | —H | 1-naphthyl | —H | —H | 1 | 1 | —(CH$_2$)$_2$— | 4 |
| 29 | biphenyl | —H | —CH$_2$CH$_2$CH$_2$CH$_2$CH$_2$CH$_3$ | —H | —H | 1 | 1 | —(CH$_2$)$_2$— | 4,4' |
| 30 | biphenyl | —H | 2-(4-tert-butylphenyl)-1,3,4-oxadiazol-5-yl-4-phenyl | —H | —H | 1 | 1 | —(CH$_2$)$_2$— | 4 |
| 31 | 4-(1H-pyrrol-1-yl)phenyl | —H | —H | —H | —H | 1 | 1 | —(CH$_2$)$_2$— | 3 |
| 32 | 4-(1H-pyrrol-1-yl)phenyl | —H | —H | —H | —H | 1 | 1 | —(CH$_2$)$_2$— | 4 |
| 33 | 4-(1H-pyrrol-1-yl)phenyl | —H | —CH$_3$ | —H | —H | 1 | 1 | —(CH$_2$)$_3$— | 4 |

-continued
| *St | Ar | R₁ | R₂ | R₃ | R₄ | X | m | T | *B.P. |
|---|---|---|---|---|---|---|---|---|---|
| 34 | 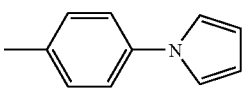 | —H | —CH₃ | —CH₃ | —H | 2 | 1 | —(CH₂)₄— | 4,4' |
| 35 | 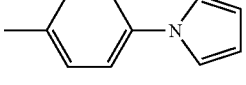 | —H | —F | —H | —H | 1 | 1 | —(CH₂)₄— | 4 |
| 36 | 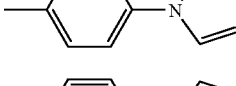 | —H | —CH₂CH₃ | —H | —H | 1 | 1 | —(CH₂)₂— | 4 |
| 37 | 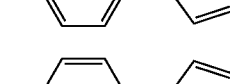 | —CH₂CH₃ | —H | —H | —H | 2 | 1 | —(CH₂)₂— | 4,4' |
| 38 | 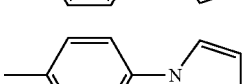 | —H | 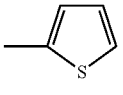 | —H | —H | 1 | 1 | —(CH₂)₂— | 4 |
| 39 | 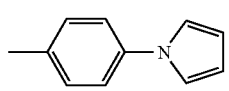 | —H | 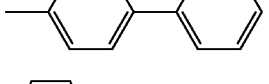 | —H | —H | 1 | 1 | —CH₂— | 4 |
| 40 | 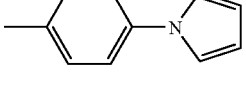 | —H | 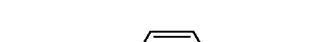 | —H | —H | 1 | 1 | —(CH₂)₂— | 4 |
| 41 | 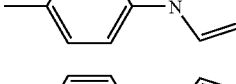 | —H |  | —H | —H | 1 | 1 | —(CH₂)₂— | 4 |
| 42 | 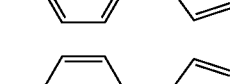 | —H | —F | —H | —H | 1 | 1 | —(CH₂)₂— | 4 |
| 43 |  | —H | —F | —F | —H | 1 | 1 | —CH₂— | 4 |
| 44 | 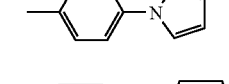 | —H | 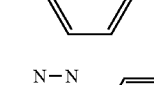 | —H | —H | 1 | 1 | —(CH₂)₆— | 4 |
| 45 | 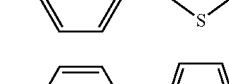 | H | 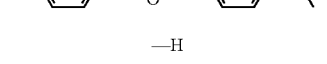 | —H | —H | 1 | 1 | —(CH₂)₂— | 4 |
| 46 | 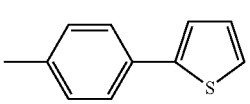 | —H | —H | —H | —H | 1 | 1 | —(CH₂)₂— | 3 |
| 47 | 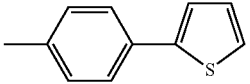 | —H | —H | —H | —H | 1 | 1 | —(CH₂)₂— | 4 |
| 48 | 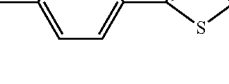 | —H | —CH₃ | —H | —H | 1 | 1 | —(CH₂)₂— | 4 |

-continued

| *St | Ar | R₁ | R₂ | R₃ | R₄ | X | m | T | *B.P. |
|---|---|---|---|---|---|---|---|---|---|
| 49 | 4-(2-thienyl)phenyl | —H | —CH₃ | —CH₃ | —H | 2 | 1 | —(CH₂)₂— | 4,4' |
| 50 | 4-(2-thienyl)phenyl | —H | —F | —H | —H | 1 | 1 | —(CH₂)₂— | 4 |
| 51 | 4-(2-thienyl)phenyl | —H | —CH₂CH₃ | —H | —H | 1 | 1 | —(CH₂)₂— | 4 |
| 52 | 4-(2-thienyl)phenyl | —CH₂CH₃ | —H | —H | —H | 2 | 1 | —(CH₂)₂— | 4,4' |
| 53 | 4-(2-thienyl)phenyl | —H | 2-thienyl | —H | —H | 1 | 1 | —(CH₂)₄— | 4 |
| 54 | 4-(2-thienyl)phenyl | —H | 4-biphenylyl | —H | —H | 1 | 1 | —(CH₂)₈— | 4 |
| 55 | 4-(2-thienyl)phenyl | —H | 5-hexyl-2-thienyl | —H | —H | 1 | 1 | —C(CH₃)₂— | 4 |
| 56 | 4-(2-thienyl)phenyl | —H | phenyl | —H | —H | 1 | 1 | —(CH₂)₈— | 4 |
| 57 | 4-(2-thienyl)phenyl | —H | —F | —H | —H | 1 | 1 | —CH(CH₃)— | 4 |
| 58 | 4-(2-thienyl)phenyl | —H | —F | —F | —H | 1 | 1 | —C(CH₃)₂CH₂— | 4 |
| 59 | 4-(2-thienyl)phenyl | —H | 1-naphthyl | —H | —H | 1 | 1 | —C(CH₃)₂— | 4 |
| 60 | 4-(2-thienyl)phenyl | —H | 2-(4-tert-butylphenyl)-1,3,4-oxadiazol-5-yl-phenyl | —H | —H | 1 | 1 | —(CH₂)₂— | 4 |
| 61 | 9,9-dimethyl-2-fluorenyl | —H | —H | —H | —H | 1 | 1 | —(CH₂)₂— | 3 |

-continued

| *St | Ar | R₁ | R₂ | R₃ | R₄ | X | m | T | *B.P. |
|---|---|---|---|---|---|---|---|---|---|
| 62 | 9,9-dimethylfluorenyl | —H | —H | —H | —H | 1 | 1 | —(CH₂)₂— | 4 |
| 63 | 9,9-dimethylfluorenyl | —H | —CH₃ | —H | —H | 1 | 1 | —(CH₂)₂— | 4 |
| 64 | 9,9-dimethylfluorenyl | —H | —CH₃ | —CH₃ | —H | 2 | 1 | —(CH₂)₂— | 4,4' |
| 65 | 9,9-dimethylfluorenyl | —H | —F | —H | —H | 1 | 1 | —(CH₂)₂— | 4 |
| 66 | 9,9-dimethylfluorenyl | —H | —CH₂CH₃ | —H | —H | 1 | 1 | —(CH₂)₄— | 4 |
| 67 | 9,9-dimethylfluorenyl | —CH₂CH₃ | —H | —H | —H | 2 | 1 | —(CH₂)₂— | 4,4' |
| 68 | 9,9-dimethylfluorenyl | —H | 2-thienyl | —H | —H | 1 | 1 | —(CH₂)₂— | 4 |
| 69 | 9,9-dimethylfluorenyl | —H | 4-biphenylyl | —H | —H | 1 | 1 | —(CH₂)₄— | 4 |
| 70 | 9,9-dimethylfluorenyl | —H | 5-hexyl-2-thienyl | —H | —H | 1 | 1 | —(CH₂)₆— | 4 |
| 71 | 9,9-dimethylfluorenyl | —H | phenyl | —H | —H | 1 | 1 | —(CH₂)₂— | 4 |

-continued
| *St | Ar | R₁ | R₂ | R₃ | R₄ | X | m | T | *B.P. |
|---|---|---|---|---|---|---|---|---|---|
| 72 |  | —H | —F | —H | —H | 1 | 1 | —(CH₂)₂— | 4 |
| 73 |  | —H | —F | —F | —H | 1 | 1 | —(CH₂)₂— | 4 |
| 74 |  | —H |  | —H | —H | 1 | 1 | —(CH₂)₄— | 4 |
| 75 |  | —H |  | —H | —H | 1 | 1 | —(CH₂)₂— | 4 |
| 76 |  | —H | —H | —H | —H | 1 | 1 | —(CH₂)₂— | 3 |
| 77 |  | —H | —H | —H | —H | 1 | 1 | —(CH₂)₂— | 4 |
| 78 |  | —H | —CH₃ | —H | —H | 1 | 1 | —(CH₂)₂— | 4 |
| 79 |  | —H | —CH₃ | —CH₃ | —H | 2 | 1 | —(CH₂)₂— | 4,4' |
| 80 |  | H | —F | —H | —H | 1 | 2 | —(CH₂)₂— | 4 |
| 81 |  | —H | —CH₂CH₃ | —H | —H | 1 | 1 | —(CH₂)₂— | 4 |
| 82 |  | —CH₂CH₃ | —H | —H | —H | 2 | 1 | —(CH₂)₂— | 4,4' |
| 83 |  | —H |  | —H | —H | 1 | 1 | —(CH₂)₂— | 4 |
| 84 |  | —H |  | —H | —H | 1 | 1 | —(CH₂)₆— | 4 |
| 85 |  | —H |  | —H | —H | 1 | 1 | —(CH₂)₂— | 4 |

-continued

| *St | Ar | R₁ | R₂ | R₃ | R₄ | X | m | T | *B.P. |
|---|---|---|---|---|---|---|---|---|---|
| 86 | 4-methylphenyl | H | phenyl | —H | —H | 1 | 1 | —(CH₂)₂— | 4 |
| 87 | 4-methylphenyl | —H | —F | —H | —H | 1 | 1 | —(CH₂)₂— | 4 |
| 88 | 4-methylphenyl | —H | —F | —F | —H | 1 | 1 | —(CH₂)₂— | 4 |
| 89 | 4-methylphenyl | —H | naphthyl | —H | —H | 1 | 1 | —(CH₂)₂— | 4 |
| 90 | 4-methylphenyl | —H | 2-(4-methylphenyl)-5-(4-tert-butylphenyl)-1,3,4-oxadiazole | —H | —H | 1 | 1 | —(CH₂)₂— | 4 |
| 91 | 4'-methoxy-3'-methylbiphenyl | —H | —H | —H | —H | 1 | 1 | —(CH₂)₂— | 3 |
| 92 | 4'-methoxy-3'-methylbiphenyl | —H | —H | —H | —H | 1 | 1 | —(CH₂)₂— | 4 |
| 93 | 4'-methoxy-3'-methylbiphenyl | —H | —CH₃ | —H | —H | 1 | 1 | —(CH₂)₂— | 4 |
| 94 | 4'-methoxy-3'-methylbiphenyl | —H | —CH₃ | —CH₃ | —H | 2 | 1 | —(CH₂)₂— | 4,4' |
| 95 | 4'-methoxy-3'-methylbiphenyl | —H | —F | —H | —H | 1 | 1 | —(CH₂)₂— | 4 |
| 96 | 4'-methoxy-3'-methylbiphenyl | —H | —CH₂CH₃ | —H | —H | 1 | 1 | —(CH₂)₂— | 4 |
| 97 | 4'-methoxy-3'-methylbiphenyl | —CH₂CH₃ | —H | —H | —H | 2 | 1 | —(CH₂)₂— | 4,4' |
| 98 | 4'-methoxy-3'-methylbiphenyl | —H | 2-thienyl | —H | —H | 1 | 1 | —(CH₂)₂— | 4 |

-continued
| *St | Ar | R$_1$ | R$_2$ | R$_3$ | R$_4$ | X | m | T | *B.P. |
|---|---|---|---|---|---|---|---|---|---|
| 99 | 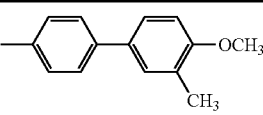 | —H | 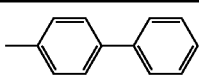 | —H | —H | 1 | 1 | —(CH$_2$)$_2$— | 4 |
| 100 | 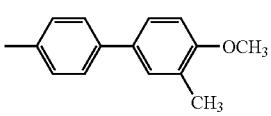 | —H | 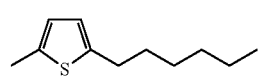 | —H | —H | 1 | 1 | —(CH$_2$)$_2$— | 4 |
| 101 | 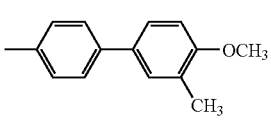 | —H |  | —H | —H | 1 | 1 | —(CH$_2$)$_2$— | 4 |
| 102 | 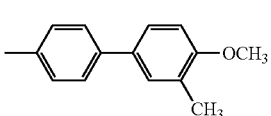 | —H | —F | —H | —H | 1 | 1 | —(CH$_2$)$_2$— | 4 |
| 103 | 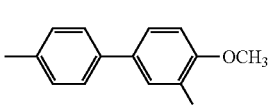 | —H | —F | —F | —H | 1 | 1 | —(CH$_2$)$_2$— | 4 |
| 104 | 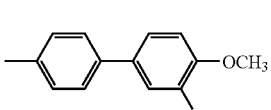 | —H | 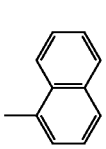 | —H | —H | 1 | 1 | —(CH$_2$)$_2$— | 4 |
| 105 | 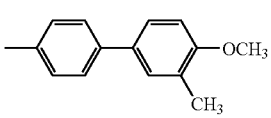 | —H | 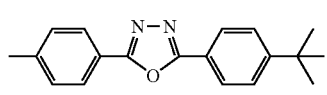 | —H | —H | 1 | 1 | —(CH$_2$)$_2$— | 4 |
| 106 | 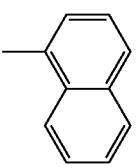 | —H | —H | —H | —H | 1 | 1 | —(CH$_2$)$_4$— | 3 |
| 107 | 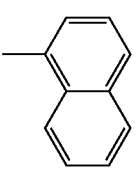 | —H | —H | —H | —H | 1 | 1 | —(CH$_2$)$_4$— | 4 |
| 108 | 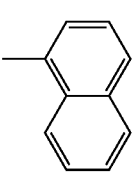 | —H | —CH$_3$ | —H | —H | 1 | 1 | —(CH$_2$)$_4$— | 4 |
| 109 | 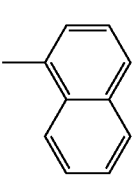 | —H | —CH$_3$ | —CH$_3$ | —H | 2 | 3 | —(CH$_2$)$_4$— | 4,4' |

-continued

| *St | Ar | R₁ | R₂ | R₃ | R₄ | X | m | T | *B.P. |
|---|---|---|---|---|---|---|---|---|---|
| 110 | 1-naphthyl | —H | —F | —H | —H | 1 | 1 | —(CH$_2$)$_4$— | 4 |
| 111 | 1-naphthyl | —H | —CH$_2$CH$_3$ | —H | —H | 1 | 1 | —(CH$_2$)$_4$— | 4 |
| 112 | 1-naphthyl | —CH$_2$CH$_3$ | —H | —H | —H | 2 | 1 | —(CH$_2$)$_8$— | 4,4' |
| 113 | 1-naphthyl | —H | 2-thienyl | —H | —H | 1 | 1 | —(CH$_2$)$_4$— | 4 |
| 114 | 1-naphthyl | —H | 4-biphenylyl | —H | —H | 1 | 2 | —C(CH$_3$)$_2$CH$_2$— | 4 |
| 115 | 1-naphthyl | —H | 5-hexyl-2-thienyl | —H | —H | 1 | 1 | —(CH$_2$)$_2$— | 4 |
| 116 | 1-naphthyl | —H | phenyl | —H | —H | 1 | 1 | —(CH$_2$)$_2$— | 4 |
| 117 | 1-naphthyl | —H | —F | —H | —H | 1 | 1 | —(CH$_2$)$_4$— | 4 |
| 118 | 1-naphthyl | —H | —F | —F | —H | 1 | 1 | —(CH$_2$)$_2$— | 4 |

-continued

| *St | Ar | R₁ | R₂ | R₃ | R₄ | X | m | T | *B.P. |
|---|---|---|---|---|---|---|---|---|---|
| 119 | 1-methylnaphthalene | —H | 1-methylnaphthalene | —H | —H | 1 | 2 | —(CH₂)₄— | 4 |
| 120 | 1-methylnaphthalene | —H | 2,5-bis(4-substituted-phenyl)-1,3,4-oxadiazole (Me, tBu) | —H | —H | 1 | 1 | —(CH₂)₄— | 4 |
| 121 | oxadiazole-Me/tBu | —H | —H | —H | —H | 1 | 1 | —(CH₂)₂— | 3 |
| 122 | oxadiazole-Me/tBu | —H | —H | —H | —H | 1 | 1 | —(CH₂)₄— | 4 |
| 123 | oxadiazole-Me/tBu | —H | —CH₃ | —H | —H | 1 | 1 | —(CH₂)₂— | 4 |
| 124 | oxadiazole-Me/tBu | —H | —CH₃ | —CH₃ | —H | 2 | 1 | —(CH₂)₂— | 4,4' |
| 125 | oxadiazole-Me/tBu | —H | —F | —H | —H | 1 | 1 | —(CH₂)₂— | 4 |
| 126 | oxadiazole-Me/tBu | —H | —CH₂CH₃ | —H | —H | 1 | 1 | —(CH₂)₂— | 4 |
| 127 | oxadiazole-Me/tBu | —CH₂CH₃ | —H | —H | —H | 2 | 1 | —(CH₂)₂— | 4,4' |
| 128 | oxadiazole-Me/tBu | —H | 2-thienyl | —H | —H | 1 | 1 | —C(CH₃)₂—CH₂— | 4 |
| 129 | oxadiazole-Me/tBu | —H | 4-biphenyl | —H | —H | 1 | 2 | —(CH₂)₈— | 4 |
| 130 | oxadiazole-Me/tBu | H | 5-hexyl-2-thienyl | —H | —H | 1 | 1 | —(CH₂)₂— | 4 |
| 131 | oxadiazole-Me/tBu | —H | phenyl | —H | —H | 1 | 1 | —(CH₂)₂— | 4 |
| 132 | oxadiazole-Me/tBu | —H | —F | —H | —H | 1 | 1 | —(CH₂)₂— | 4 |
| 133 | oxadiazole-Me/tBu | —H | —F | —F | —H | 1 | 1 | —(CH₂)₂— | 4 |

-continued

| *St | Ar | R₁ | R₂ | R₃ | R₄ | X | m | T | *B.P. |
|---|---|---|---|---|---|---|---|---|---|
| 134 | 2-(4-tert-butylphenyl)-5-phenyl-1,3,4-oxadiazole | —H | 8-methylnaphthalen-1-yl | —H | —H | 1 | 1 | —C(CH₃)₂—CH₂— | 4 |
| 135 | 2-(4-tert-butylphenyl)-5-phenyl-1,3,4-oxadiazole | —H | 2-(4-tert-butylphenyl)-5-phenyl-1,3,4-oxadiazole | —H | —H | 1 | 1 | —(CH₂)₂— | 4 |
| 136 | 4-(diphenylamino)phenyl | —H | —H | —H | —H | 1 | 1 | —(CH₂)₂— | 3 |
| 137 | 4-(diphenylamino)phenyl | —H | —H | —H | —H | 1 | 1 | —(CH₂)₂— | 4 |
| 138 | 4-(diphenylamino)phenyl | —H | —CH₃ | —H | —H | 1 | 1 | —(CH₂)₂— | 4 |
| 139 | 4-(diphenylamino)phenyl | —H | —CH₃ | —CH₃ | —H | 2 | 1 | —(CH₂)₂— | 4,4' |
| 140 | 4-(diphenylamino)phenyl | —H | —F | —H | —H | 1 | 1 | —(CH₂)₂— | 4 |

-continued
| *St | Ar | R₁ | R₂ | R₃ | R₄ | X | m | T | *B.P. |
|---|---|---|---|---|---|---|---|---|---|
| 141 | 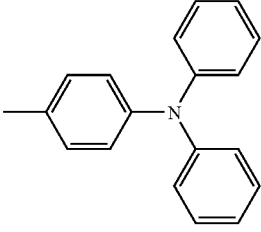 | —H | —CH₂CH₃ | —H | —H | 1 | 1 | —(CH₂)₂— | 4 |
| 142 | 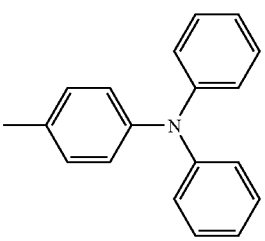 | —CH₂CH₃ | —H | —H | —H | 2 | 1 | —(CH₂)₂— | 4,4' |
| 143 | 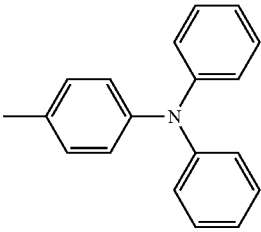 | —H | 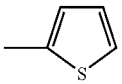 | —H | —H | 1 | 1 | —(CH₂)₂— | 4 |
| 144 | 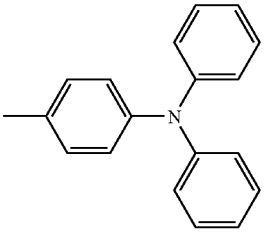 | —H | 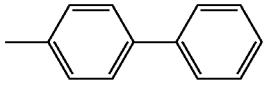 | —H | —H | 1 | 1 | —(CH₂)₂— | 4 |
| 145 | 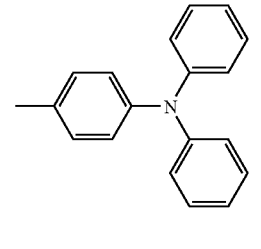 | —H | 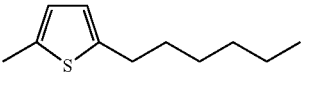 | —H | —H | 1 | 1 | —(CH₂)₂— | 4 |
| 146 | 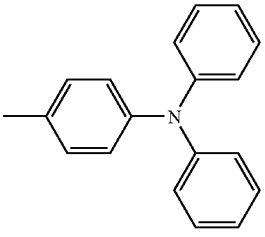 | —H | 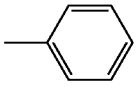 | —H | —H | 1 | 1 | —(CH₂)₂— | 4 |

-continued
| *St | Ar | R₁ | R₂ | R₃ | R₄ | X | m | T | *B.P. |
|---|---|---|---|---|---|---|---|---|---|
| 147 | 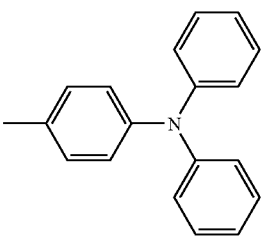 | —H | —F | —H | —H | 1 | 1 | —(CH₂)₂— | 4 |
| 148 | 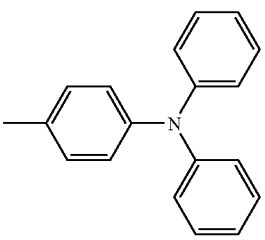 | —H | —F | —F | —H | 1 | 1 | —(CH₂)₂— | 4 |
| 149 | 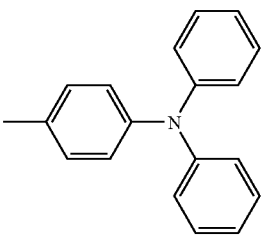 | —H | 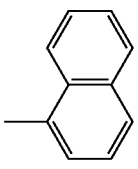 | —H | —H | 1 | 1 | —(CH₂)₂— | 4 |
| 150 | 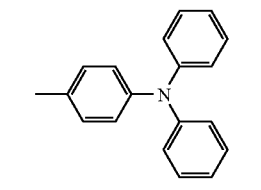 | —H | 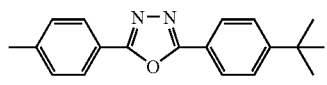 | —H | —H | 1 | 1 | —CH₂— | 4 |
| 151 | 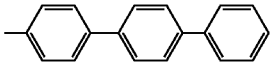 | —H | —H | —H | —H | 1 | 1 | —(CH₂)₈— | 3 |
| 152 | 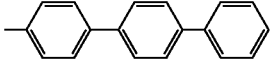 | —H | —H | —H | —H | 1 | 1 | —(CH₂)₆— | 4 |
| 153 | 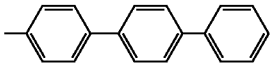 | —H | —CH₃ | —H | —H | 1 | 1 | $-\underset{\underset{CH_3}{\mid}}{CH}-CH_2-CH_2-$ | 4 |
| 154 | 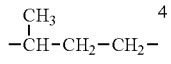 | —H | —CH₃ | —CH₃ | —H | 2 | 1 | —(CH₂)₈— | 4,4' |
| 155 | 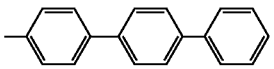 | —H | —F | —H | —H | 1 | 1 | —(CH₂)₆— | 4 |
| 156 | 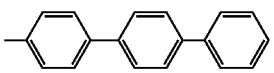 | —H | —CH₂CH₃ | —H | —H | 1 | 1 | —(CH₂)₆— | 4 |
| 157 | 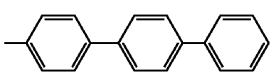 | —CH₂CH₃ | —H | —H | —H | 2 | 1 | —(CH₂)₆— | 4,4' |
| 158 | 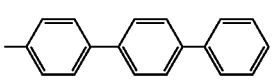 | —H | 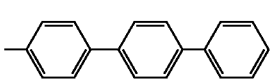 | —H | —H | 1 | 1 | —(CH₂)₆— | 4 |

-continued
| *St | Ar | R₁ | R₂ | R₃ | R₄ | X | m | T | *B.P. |
|---|---|---|---|---|---|---|---|---|---|
| 159 | 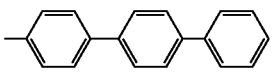 | —H | 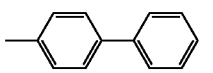 | —H | —H | 1 | 2 | —(CH₂)₈— | 4 |
| 160 | 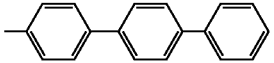 | —H | 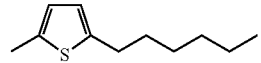 | —H | —H | 1 | 1 | —(CH₂)₆— | 4 |
| 161 | 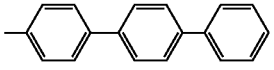 | —H |  | —H | —H | 1 | 1 | —(CH₂)₆— | 4 |
| 162 | 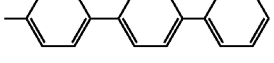 | —H | —F | —H | —H | 1 | 1 | —(CH₂)₆— | 4 |
| 163 | 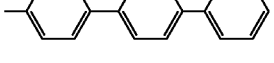 | —H | —F | —F | —H | 1 | 1 | —(CH₂)₆— | 4 |
| 164 | 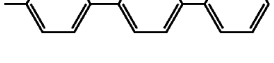 | —H | 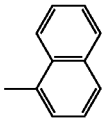 | —H | —H | 1 | 1 | —(CH₂)₈— | 4 |
| 165 | 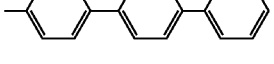 | —H | 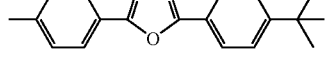 | —H | —H | 1 | 1 | —(CH₂)₆— | 4 |
| 166 | 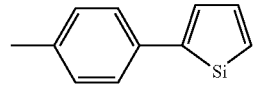 | —H | —H | —H | —H | 1 | 1 | —(CH₂)₈— | 3 |
| 167 | 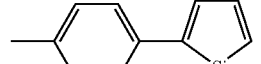 | —H | —H | —H | —H | 1 | 1 | —(CH₂)₂— | 4 |
| 168 | 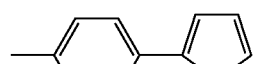 | —H | —CH₃ | —H | —H | 1 | 1 | —(CH₂)₂— | 4 |
| 169 | 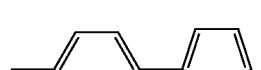 | —H | —CH₃ | —CH₃ | —H | 2 | 1 | —(CH₂)₂— | 4,4' |
| 170 | 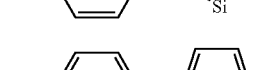 | —H | —F | —H | —H | 1 | 1 | —(CH₂)₂— | 4 |
| 171 | 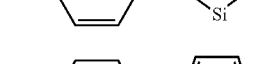 | —H | —CH₂CH₃ | —H | —H | 1 | 1 | —(CH₂)₂— | 4 |
| 172 | 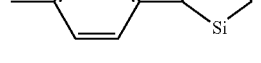 | —CH₂CH₃ | —H | —H | —H | 2 | 1 | —(CH₂)₂— | 4,4' |
| 173 | 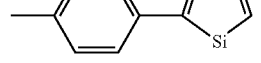 | —H |  | —H | —H | 1 | 1 | —(CH₂)₈— | 4 |
| 174 | 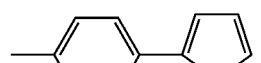 | —H | 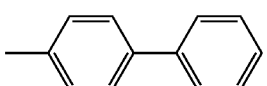 | —H | —H | 1 | 2 | —(CH₂)₈— | 4 |

-continued

| *St | Ar | R₁ | R₂ | R₃ | R₄ | X | m | T | *B.P. |
|---|---|---|---|---|---|---|---|---|---|
| 175 | 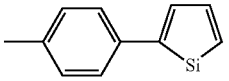 | —H | 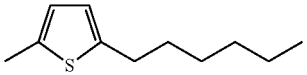 | —H | —H | 1 | 1 | —(CH₂)₈— | 4 |
| 176 | 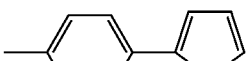 | —H | 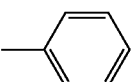 | —H | —H | 1 | 1 | —(CH₂)₂— | 4 |
| 177 | 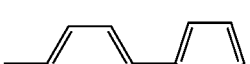 | —H | —F | —H | —H | 1 | 1 | —(CH₂)₂— | 4 |
| 178 | 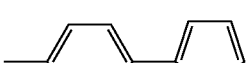 | —H | —F | —F | —H | 1 | 1 | —(CH₂)₂— | 4 |
| 179 | 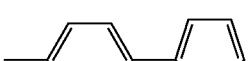 | —H | 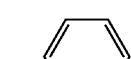 | —H | —H | 1 | 1 | —(CH₂)₂— | 4 |
| 180 | 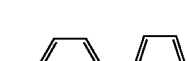 | —H | 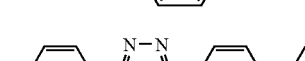 | —H | —H | 1 | 1 | —(CH₂)₂— | 4 |

*St = Structure,
*B.P. = Binding Position

Examples of the charge-transporting polyester having repeating structures containing, as a partial structure, at least one structure selected from the structures represented by the formula (I-1) include polyesters represented by the following formula (II-1) and polyesters represented by the following formula (II-2):

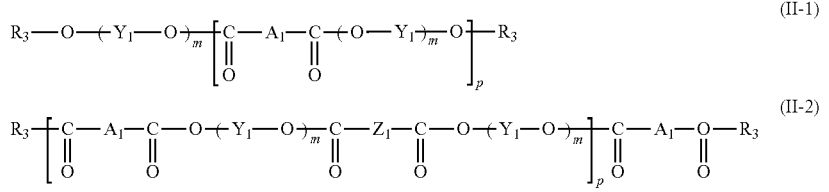

In the formulae (II-1) and (II-2), $A_1$ represents at least one structure selected from the structures represented by the formula (I-1); $Y_1$ represents a divalent alcohol residue; $Z_1$ represents a divalent carboxylic acid residue; m represents an integer of 1 to 5; p represents an integer of 5 to 5000; and $R_3$s each independently represent a hydrogen atom, —O—($Y_1$—O)$_m$—H, and —O—($Y_1$—O)$_m$—CO—$Z_1$—CO—OR' wherein R' represents a hydrogen atom, an alkyl group, a substituted or unsubstituted aryl group, or a substituted or unsubstituted aralkyl group, and $Y_1$, $Z_1$ and m have the same meanings as defined above. Examples of the aryl group and aralkyl group are as described above.

In the formulae (II-1) and (II-2), $A_1$ represents at least one structure selected from the structures represented by the formula (I-1), and a plurality of $A_1$s present in a charge-transporting polyester represented by the formula (II-1) or (II-2) may have the same structure or different structures.

In the formulae (II-1) and (II-2), specific examples of $Y_1$ and $Z_1$ include groups selected from the following formulae (1) to (6):

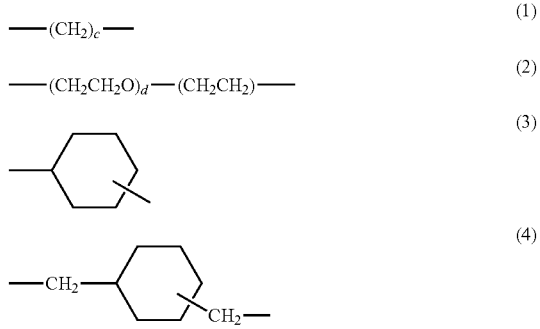

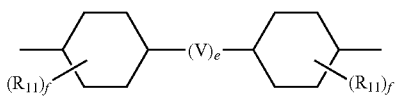
(5)

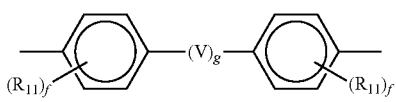
(6)

In the formulae (1) to (6), $R_{11}$ represents a hydrogen atom, an alkyl group having 1 to 20 carbon atoms, an alkoxy group having 1 to 4 carbon atoms, a substituted or unsubstituted phenyl group, a substituted or unsubstituted aralkyl group, or a halogen atom wherein examples of a substituent that can be substituted on each group include the substituents described above; c and d each represent an integer of 1 to 10; e and g each represent 0 or 1; f represents an integer of 0 to 6; and V may be a group selected from the following (7) to (17):

 (7)

 (8)

 (9)

 (10)

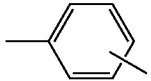 (11)

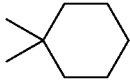 (12)

 (13)

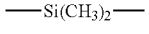 (14)

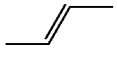 (15)

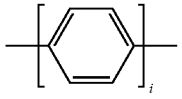 (16)

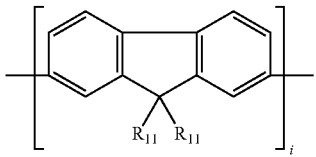 (17)

In the formulae (7) to (17), h and i each independently represents an integer of 1 to 10, and $R_{11}$ has the same meaning as defined above.

The charge-transporting polyester may be constituted as follows.

In the formula (I-1):
$R_1$, $R_2$, $R_3$ and $R_4$ each represent a hydrogen atom, a methyl group, a phenyl group, an ethyl group, a hexyl group, a biphenyl group, a naphthyl group, a thienyl group, or a fluorine atom;

Ar represents a phenyl group, a biphenyl group, a toluyl group, a methoxy group, a 9,9-dimethyl-2-fluorenyl group, a triphenylamino group, a pyrrole group, a terphenyl group, or a 2-phenyl-5-p-tert-butylphenyl(1,3,4)oxadiazole group;

x represents an integer of 1 to 2;

T represents a methylene group, an ethylene group, a butylene group, a hexylene group or an isopropylene group; and m represents an integer of 1.

In the formulae (II-1) and (II-2):
$A_1$ represents at least one structure selected from the structures represented by the formula (I-1);

$Y_1$ represents a methylene group, an ethylene group, a phenylene group or a hexylene group;

$Z_1$ represents a methylene group, an ethylene group, a phenylene group or a hexylene group;

m represents an integer of 1 to 2;

p represents an integer of 10 to 1000; and $R_3$ represents a hydrogen atom, a methyl group or a phenyl group.

The charge-transporting polyester is more preferably constituted as follows.

In the formula (I-1):
$R_1$, $R_2$, $R_3$ and $R_4$ each represent a hydrogen atom, a methyl group, a phenyl group or a fluorine atom;

Ar represents a phenyl group, a biphenyl group, a pyrrole group, a 9,9-dimethyl-2-fluorenyl group or a 2-phenyl-5-p-tert-butylphenyl(1,3,4)oxadiazole group;

x represents an integer of 1;

T represents an ethylene group; and m represents an integer of 1.

In the formulae (II-1) and (II-2):
$A_1$ represents at least one structure selected from the structures represented by the formula (I-1);

$Y_1$ represents an ethylene group or a hexylene group;

$Z_1$ represents an ethylene group;

m represents an integer of 1 to 2;

p represents an integer of 10 to 500; and $R_3$ represents a hydrogen atom.

Hereinafter, specific examples of the charge-transporting polyesters represented by the formulae (II-1) and (II-2) will be listed below, but the invention is not limited by these specific examples.

The numbers in the column for monomer $A_1$ in the following Tables correspond to the structure numbers of the specific examples of the structures represented by the formula (I-1). The polymers having "-" in column $Z_1$ are specific examples of the charge-transporting polyester represented by the formula (II-1), and the other polymers are specific examples of the charge-transporting polyester represented by formula (II-2). Each specific example of the charge-transporting polyester has an identification number in the following Tables, and a specific example with a number of 15 for example will be called "exemplary compound (15)" hereinafter. The terminal groups $R_3$ each independently represent a hydrogen or a group represented by —O—$(Y_1$—O$)_m$—H or —O—$(Y_1$—O$)_m$—CO—$Z_1$CO—OR' wherein R' represents a hydrogen atom, an alkyl group, a substituted or unsubstituted aryl group or a substituted or unsubstituted aralkyl group, and $Y_1$, $Z_1$ and m have the same meanings as defined above.

| Polymer | *A₁ (I-1) | Ratio | Y₁ | Z₁ | m | P |
|---|---|---|---|---|---|---|
| 1 | 2 | — | —(CH₂)₂— | — | 1 | 76 |
| 2 | 2 | — | ⌬ (1,4-cyclohexylene) | —(CH₂)₂— | 1 | 65 |
| 3 | 2 | — | phenyl-CH₂-phenyl | — | 1 | 55 |
| 4 | 2 | — | cyclohexyl-CH₂-cyclohexyl | — | 1 | 53 |
| 5 | 2 | — | 1,3-phenylene | cyclohexyl-CH₂-cyclohexyl | 1 | 78 |
| 6 | 2 | — | 1,4-diethylcyclohexyl | — | 1 | 66 |
| 7 | 2 | — | —CH₂-(1,3-phenylene)-CH₂— | — | 1 | 64 |
| 8 | 2 | — | —(CH₂)₆— | — | 1 | 82 |
| 9 | 16 | — | —(CH₂)₂— | — | 1 | 86 |
| 10 | 16 | — | 1,4-cyclohexylene | — | 1 | 51 |
| 11 | 16 | — | phenyl-CH₂-phenyl | — | 1 | 49 |
| 12 | 16 | — | cyclohexyl-CH₂-cyclohexyl | — | 1 | 73 |
| 13 | 16 | — | 1,3-phenylene | — | 1 | 86 |
| 14 | 16 | — | 1,4-diethylcyclohexyl | — | 1 | 49 |
| 15 | 16 | — | —CH₂-(1,3-phenylene)-CH₂— | — | 1 | 57 |
| 16 | 16 | — | —(CH₂)₆— | — | 1 | 71 |
| 17 | 17 | — | —(CH₂)₂— | — | 1 | 80 |

-continued
| Polymer | *A₁ (I-1) | Ratio | Y₁ | Z₁ | m | P |
|---|---|---|---|---|---|---|
| 18 | 17 | — | 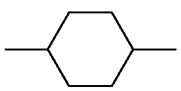 | — | 1 | 90 |
| 19 | 17 | — | 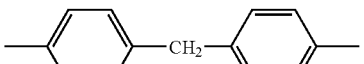 | — | 1 | 65 |
| 20 | 17 | — | 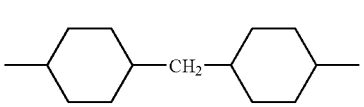 | — | 1 | 78 |
| 21 | 17 | — | 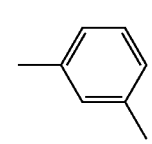 | — | 1 | 78 |
| 22 | 17 | — |  | — | 1 | 75 |
| 23 | 17 | — | 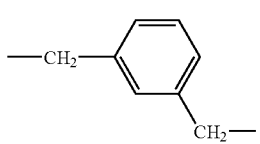 | — | 1 | 46 |
| 24 | 17 | — | —(CH₂)₆— | — | 1 | 69 |
| 25 | 25 | — | —(CH₂)₂— | — | 1 | 72 |
| 26 | 25 | — | 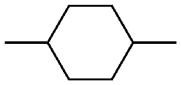 | — | 1 | 76 |
| 27 | 25 | — | 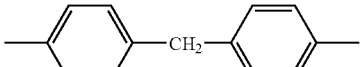 | 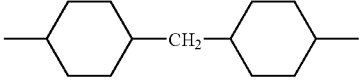 | 1 | 80 |
| 28 | 25 | — | 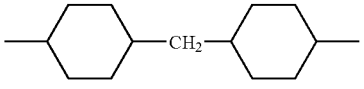 | — | 1 | 96 |
| 29 | 25 | — | 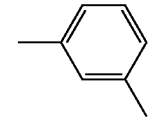 | — | 1 | 102 |
| 30 | 25 | — |  | — | 1 | 79 |
| 31 | 25 | — | 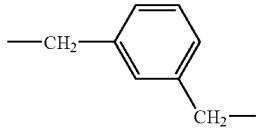 | — | 1 | 68 |
| 32 | 25 | — | —(CH₂)₆— | — | 1 | 61 |
| 33 | 32 | — | —(CH₂)₂— | — | 1 | 59 |
| 34 | 32 | — | 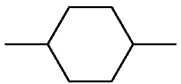 | — | 1 | 49 |

-continued

| Polymer | *$A_1$ (I-1) | Ratio | $Y_1$ | $Z_1$ | m | P |
|---|---|---|---|---|---|---|
| 35 | 32 | — | -C6H4-CH2-C6H4- | — | 1 | 58 |
| 36 | 32 | — | -C6H10-CH2-C6H10- | — | 1 | 67 |
| 37 | 32 | — | 1,3-phenylene | — | 1 | 89 |
| 38 | 32 | — | 1,4-cyclohexylene-bis(ethylene) | — | 1 | 57 |
| 39 | 32 | — | -CH2-(1,3-C6H4)-CH2- | — | 1 | 58 |
| 40 | 32 | — | —(CH$_2$)$_6$— | — | 1 | 86 |
| 41 | 47 | — | —(CH$_2$)$_2$— | — | 1 | 84 |
| 42 | 47 | — | 1,4-cyclohexylene | — | 1 | 93 |
| 43 | 47 | — | -C6H4-CH2-C6H4- | — | 1 | 97 |
| 44 | 47 | — | -C6H10-CH2-C6H10- | — | 1 | 82 |
| 45 | 47 | — | 1,3-phenylene | — | 1 | 58 |
| 46 | 47 | — | 1,4-cyclohexylene-bis(ethylene) | — | 1 | 50 |
| 47 | 47 | — | -CH2-(1,3-C6H4)-CH2- | — | 1 | 79 |
| 48 | 47 | — | —(CH$_2$)$_6$— | — | 1 | 78 |
| 49 | 47 | — | —(CH$_2$)$_2$— | — | 1 | 49 |
| 50 | 47 | — | 1,4-cyclohexylene | — | 1 | 100 |
| 51 | 47 | — | -C6H4-CH2-C6H4- | — | 1 | 92 |

-continued

| Polymer | *A₁ (I-1) | Ratio | Y₁ | Z₁ | m | P |
|---|---|---|---|---|---|---|
| 52 | 47 | — | -cyclohexyl-CH₂-cyclohexyl- | — | 1 | 94 |
| 53 | 47 | — | 1,3-phenylene | — | 1 | 80 |
| 54 | 47 | — | -CH₂CH₂-cyclohexyl-CH₂CH₂- | — | 1 | 86 |
| 55 | 47 | — | -CH₂-(1,3-phenylene)-CH₂- | — | 1 | 94 |
| 56 | 47 | — | —(CH₂)₆— | —(CH₂)₂— | 1 | 96 |
| 57 | 63 | — | —(CH₂)₂— | — | 1 | 92 |
| 58 | 63 | — | 1,4-cyclohexylene | — | 1 | 80 |
| 59 | 63 | — | -phenyl-CH₂-phenyl- | — | 1 | 72 |
| 60 | 63 | — | -cyclohexyl-CH₂-cyclohexyl- | -phenyl-CH₂-phenyl- | 1 | 79 |
| 61 | 63 | — | 1,3-phenylene | — | 1 | 78 |
| 62 | 63 | — | -CH₂CH₂-cyclohexyl-CH₂CH₂- | — | 1 | 98 |
| 63 | 63 | — | -CH₂-(1,3-phenylene)-CH₂- | — | 1 | 97 |
| 64 | 63 | — | —(CH₂)₆— | — | 1 | 82 |
| 65 | 73 | — | —(CH₂)₂— | — | 1 | 97 |
| 66 | 73 | — | 1,4-cyclohexylene | — | 1 | 92 |
| 67 | 73 | — | -phenyl-CH₂-phenyl- | — | 1 | 68 |
| 68 | 73 | — | -cyclohexyl-CH₂-cyclohexyl- | — | 1 | 69 |

-continued

| Polymer | *A₁ (I-1) | Ratio | Y₁ | Z₁ | m | P |
|---|---|---|---|---|---|---|
| 69 | 73 | — | 1,3-phenylene | 4,4'-methylenediphenylene | 1 | 98 |
| 70 | 73 | — | 1,4-bis(ethyl)cyclohexylene | — | 1 | 79 |
| 71 | 73 | — | 1,3-bis(methylene)phenylene | — | 1 | 88 |
| 72 | 73 | — | —(CH₂)₆— | — | 1 | 86 |
| 73 | 79 | — | —(CH₂)₂— | — | 1 | 66 |
| 74 | 79 | — | 1,4-cyclohexylene | — | 1 | 63 |
| 75 | 79 | — | 4,4'-methylenediphenylene | — | 1 | 70 |
| 76 | 79 | — | 4,4'-methylenedicyclohexylene | — | 1 | 74 |
| 77 | 79 | — | 1,3-phenylene | — | 1 | 75 |
| 78 | 79 | — | 1,4-bis(ethyl)cyclohexylene | — | 1 | 83 |
| 79 | 79 | — | 1,3-bis(methylene)phenylene | — | 1 | 82 |
| 80 | 79 | — | —(CH₂)₆— | — | 1 | 96 |
| 81 | 93 | — | —(CH₂)₂— | — | 1 | 56 |
| 82 | 116 | — | —(CH₂)₂— | — | 1 | 50 |
| 83 | 133 | — | —(CH₂)₂— | — | 1 | 80 |
| 84 | 137 | — | —(CH₂)₂— | — | 1 | 91 |
| 85 | 137 | — | 1,4-cyclohexylene | — | 1 | 97 |
| 86 | 137 | — | 4,4'-methylenediphenylene | — | 1 | 85 |
| 87 | 137 | — | 4,4'-methylenedicyclohexylene | — | 1 | 82 |

-continued

| Polymer | *A₁ (I-1) | Ratio | Y₁ | Z₁ | m | P |
|---|---|---|---|---|---|---|
| 88 | 137 | — | 1,3-dimethylphenylene | — | 1 | 79 |
| 89 | 137 | — | 1,4-bis(ethyl)cyclohexylene | — | 1 | 90 |
| 90 | 137 | — | —CH₂—(1,3-phenylene)—CH₂— | — | 1 | 105 |
| 91 | 137 | — | —(CH₂)₆— | —(CH₂)₂— | 1 | 106 |
| 92 | 145 | — | 1,3-dimethylphenylene | — | 1 | 85 |
| 93 | 145 | — | 1,4-bis(ethyl)cyclohexylene | — | 1 | 107 |
| 94 | 145 | — | —CH₂—(1,3-phenylene)—CH₂— | — | 1 | 56 |
| 95 | 145 | — | —(CH₂)₆— | — | 1 | 49 |
| 96 | 153 | — | —(CH₂)₂— | — | 1 | 82 |
| 97 | 167 | — | —(CH₂)₂— | — | 1 | 85 |
| 98 | 2/16 | 1/1 | —(CH₂)₂— | — | 1 | 38 |
| 99 | 16/17 | 1/1 | —(CH₂)₂— | — | 1 | 48 |
| 100 | 16/25 | 1/1 | —(CH₂)₂— | — | 1 | 40 |
| 101 | 16/32 | 2/1 | —(CH₂)₂— | — | 1 | 38 |
| 102 | 2/17/32 | 1/1/1 | —(CH₂)₂— | — | 1 | 58 |

*A₁ (I-1) = Structure No. of A₁ in formula (I-1)

The weight-average molecular weight Mw of the charge-transporting polyester may be in the range of 5,000 to 300,000. The glass transition point (Tg) of the charge-transporting polyester may be 60° C. or more.

The weight-average molecular weight Mw may be determined by the following method. That is, the weight-average molecular weight Mw is determined by preparing a THF solution of 1.0 mass % charge-transporting polyester and then analyzing the solution by gel permeation chromatography (GPC) in a differential refractometer (RI) while using styrene polymers as the standard sample.

The glass transition point is determined with a differential scanning calorimeter with α-Al₂O₃ as the reference by heating the sample to increase its temperature until it becomes rubbery, then rapidly cooling it in liquid nitrogen, and heating it again at an increasing temperature rate of 10° C./min. during which the glass transition point is measured.

Hereinafter, a method of synthesizing the charge-transporting polyester is described.

The method of synthesizing the charge-transporting polyester is not particularly limited, and a combination of known methods may be used in accordance with a desired structure.

The method of synthesizing the charge-transporting polyester consisting of repeating units containing, as a partial structure, at least one structure selected from the structures represented by the formula (I-1) will be described in detail in the following specific example wherein the charge-transporting polyester is a charge-transporting polyester represented by the formula (II-1) or (II-2).

When the charge-transporting polyester is a charge-transporting polyester represented by the formula (II-1) or (II-2), it is synthesized by polymerizing a monomer represented by the following formula (I-2) by a known method described in, for example, Experimental Chemical Lecture (Jikken Kagaku Kouza) 4th ed., vol. 28 (Maruzen Co., Ltd., 1992).

$$A'-A_1-A' \quad (I\text{-}2)$$

In the formula (I-2), $A_1$ represents at least one structure selected from the structures represented by the formula (I-1); A' represents a hydroxyl group, a halogen atom, or —O—R₅ group wherein R₅ represents an alkyl group, a substituted or unsubstituted aryl group or an aralkyl group.

Specifically, for example, the monomer represented by the formula (I-2) may be synthesized as follows.

By using a known method, substituted or unsubstituted 1,2-phenylenediamine and 4,4'-dibromobenzil are allowed to react in the presence of a weak base such as pyridine or triethylamine and an alcohol solvent at room temperature (25° C.) to synthesize a quinoxaline skeleton. Separately, methyl iodophenylpropionate and an amine compound are subjected to Ullmann reaction to synthesize a diarylamine. The monomer $A_1$ represented by the formula (I-2) is obtained through the palladium coupling reaction of the quinoxaline skeleton with the diarylamine. However, the method of synthesizing the monomer represented by the formula (I-2) is not limited to this example.

Using the monomer represented by the formula (I-2), the charge-transporting polyester is synthesized in the following manner.

When A' is a hydroxyl group, the monomer is mixed with an equivalent amount of dihydric alcohol represented by $HO-(Y_1-O)_m-H$ ($Y_1$ and m have the same meanings as those of $Y_1$ and m in the formulae (II-1) and (II-2), the same applies hereinafter) and polymerized in the presence of an acid catalyst. The acid catalyst includes catalysts used in ordinary esterification reaction, such as sulfuric acid, toluenesulfonic acid and trifluoroacetic acid, and the catalyst is used in the range of 1/10,000 to 1/10 parts by weight, preferably 1/1,000 to 1/50 parts by weight, based on 1 part by weight of the monomer. A solvent capable of forming an azeotrope with water may be used for eliminating water formed during the polymerization. Effective solvents include toluene, chlorobenzene, and 1-chloronaphthalene, and the amount of solvent to be used may be in the range of 1 to 100 parts by weight, preferably 2 to 50 parts by weight, based on 1 part by weight of the monomer. The reaction temperature may be selected arbitrarily, but the reaction is preferably carried out at the boiling point of the solvent in order to eliminate the water generated in the polymerization.

After the reaction, if a solvent is not used, the product may be dissolved in a solvent that can dissolve the product. If a solvent is used, the reaction solution, as it is, is added dropwise to a poor solvent in which the polymer is not easily dissolved (e.g., an alcohol such as methanol or ethanol, or an acetone), thereby precipitating the polyester, and the polyester is separated and then sufficiently washed with water or an organic solvent, and dried. If necessary, there may be repeated a reprecipitation process of dissolving the polyester in an appropriate organic solvent and adding it dropwise into a poor solvent thereby precipitating the polyester. Such a reprecipitation process may be conducted under efficient agitation for example with a mechanical stirrer. The solvent for dissolving the polyester at the time of the reprecipitation process is used preferably in the range of 1 to 100 parts by weight, more preferably 2 to 50 parts by weight, based on 1 part by weight of the polyester. The poor solvent is used preferably in the range of 1 to 1,000 parts by weight, more preferably 10 to 500 parts by weight, based on 1 part by weight of the polyester.

If A' represents $-O-R_5$, the polyester may be synthesized by adding to the monomer an excessive amount of dihydric alcohol represented by $HO-(Y_1-O)_m-H$, and heating the mixture with a catalyst such as an inorganic acid (e.g. sulfuric acid or phosphoric acid), titanium alkoxide, an acetate or carbonate (e.g., an acetate or carbonate of calcium or cobalt), or an oxide of zinc or lead, so as to cause ester exchange. The dihydric alcohol is used in an amount in the range of 2 to 100 equivalents, preferably 3 to 50 equivalents, based on 1 equivalent of the monomer. The catalyst is used in an amount in the range of 1/10,000 to 1 parts by weight, preferably 1/1,000 to 1/2 part by weight, based on 1 part by weight of the monomer. The reaction may be carried out at a reaction temperature of 200 to 300° C., and after completion of ester exchange from the group $-O-R_6$ to the group $-O-(Y_1-O)_m-H$, the reaction may be carried out under reduced pressure so as to accelerate the polymerization reaction through elimination of the group $HO-(Y_1-O)_m-H$. The reaction may be carried out in a high-boiling solvent azeotropic with $HO-(Y_1-O)_m-H$, such as 1-chloronaphthalene, while $HO-(Y_1O)_m-H$ is removed by azeotropy at normal pressures.

Alternatively, the charge-transferring polyester may be synthesized in the following manner. In each of the cases described above, the reaction may be performed by adding a dihydric alcohol in excess, to generate a compound represented by the following formula (I-3), and this compound may be used in place of the monomer represented by the formula (I-2) and allowed to react with a divalent carboxylic acid or a divalent carboxylic acid halide in the same manner as described above (with respect to the case where A' represents $-O-R_5$), whereby the polyester may be obtained.

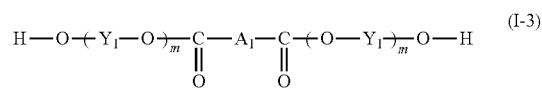
(I-3)

In the formula (I-3), $A_1$ represents at least one structure selected from the structures represented by the formula (I-1); $Y_1$ represents a divalent alcohol residue; and m represents an integer of 1 to 5.

An arbitrary molecule may be introduced into the terminal of the charge-transporting polyester. In this case, the following method may be mentioned. That is, when A' in the monomer represented by the formula (I-2) represents a hydroxyl group, the monomer may be copolymerized with a monocarboxylic acid as a compound to be introduced into the terminal, or alternatively the compound obtained by the polymerization reaction of the polymer may be allowed react with a monocarboxylic acid, thereby introducing the monocarboxylic acid into the terminal of the polyester.

When A' represents a halogen, the monomer may be copolymerized with a monoacid chloride as a compound to be introduced into the terminal, or the polymer obtained by the polymerization reaction may be allowed to react with a monoacid chloride as a compound to be introduced into the terminal, thereby introducing the monoacid chloride into the terminal of the polyester. When A' represents $-O-R_5$, the monomer may be copolymerized with a monoester as a compound to be introduced into the terminal, or the polymer obtained by the polymerization reaction may be allowed react with a monoester as a compound to be introduced into the terminal, thereby introducing the monoester into the terminal of the polyester.

The structure of the organic luminescence element in the exemplary embodiment will now be described in detail.

The layer structure of the organic electroluminescence element in the exemplary embodiment is not particularly limited insofar as it includes a pair of electrodes at least one of which is transparent or semitransparent, and one or more organic compound layers disposed between the pair of electrodes, wherein at least one of the organic compound layers includes at least one charge-transporting polyester described above.

In the organic electroluminescence element in the exemplary embodiment wherein the number of the organic compound layers is 1, the organic compound layer refers to a light-emitting layer having a charge transporting ability, and the light-emitting layer contains the above charge-transporting polyester. When the organic compound layer is composed exclusively of a light-emitting layer, the area of the element may be easily increased and the production of the element may be easy as compared with other layer structures. This is because the number of layer is small, and the layer may be manufactured for example by wet coating or the like.

When there are plural organic layers (that is, in the case of a function separation type where the respective layers have different functions), at least one of the layers is a light-emitting layer, and this light-emitting layer may be a light-emitting layer having a charge transporting ability. In this case, specific examples of the layer structure including the light-emitting layer or the light-emitting layer having a charge transporting ability, and one or more other layers include the following (1) to (3):

(1) A layer structure having a light-emitting layer and at least one layer selected from an electron-transporting layer and an electron injection layer. This structure, having a light-emitting layer and at least one layer selected from an electron-transporting layer and an electron injection layer, may achieve a balance of easy production and light emitting efficiency, as compared with other layer structures. This is supposedly because the number of the layers is small as compared with a layer structure in which functions are fully separated to different layers, and the injection efficiency of electrons, which generally have a lower mobility than holes, is improved to realize the balance of charge in the light-emitting layer.

(2) A layer structure having (i) at least one layer selected from a hole-transporting layer and a bole injection layer, (ii) a light-emitting layer, and (iii) at least one layer selected from an electron-transporting layer and an electron injection layer. This structure, having at least one layer selected from a hole-transporting layer and a hole injection layer, a light-emitting layer, and at least one layer selected from an electron-transporting layer and an electron injection layer, may achieve excellent light emitting efficiency and low-voltage driving as compared with other layer structures. This is supposedly because as compared with other layer structures, this structure in which the functions are fully separated to different layers may maximize the injection efficiency of charges, which are to be recombined in the light-emitting layer.

(3) A layer structure having at least one layer selected from a hole-transporting layer and a hole injection layer, and a light-emitting layer. This layer structure, having a light-emitting layer and at least one layer selected from a hole-transporting layer and a hole injection layer, may achieve a balance of easy production and light emitting efficiency, as compared with other layer structures. This is supposedly because the number of the layers is small as compared with a layer structure in which functions are fully separated to different layers, the injection efficiency of holes into the light-emitting layer is improved, and the injection of excessive electrons into the light-emitting layer is suppressed.

The other layers than the light-emitting layer (or the light-emitting layer having a charge transporting ability) in these layer structures (1) to (3) have a function as either a charge-transporting layer or a charge injection layer. In any of the layer structures (1) to (3), there is a layer containing the charge-transporting polyester.

In the organic electroluminescence element in the exemplary embodiment, the light-emitting layer, the hole-transporting layer, the hole injection layer, the electron-transporting layer, and the electron injection layer may further contain a charge-transporting compound (hole-transporting material, electron-transporting material) other than the charge-transporting polyester. Details of this charge-transporting compound are described later.

Figure 2:
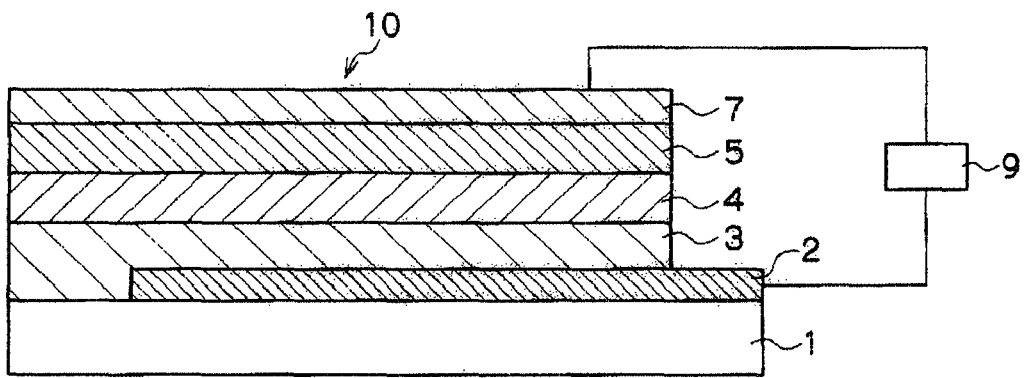
FIG. 2 is a schematic diagram showing a display device in another exemplary embodiment.
Figure 3:
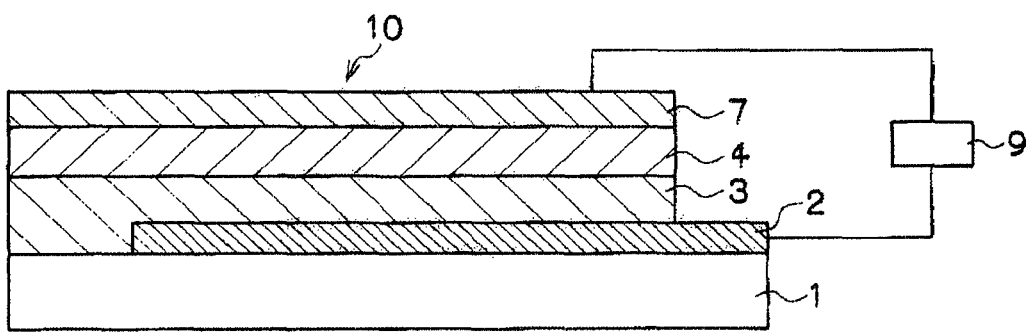
FIG. 3 is a schematic diagram showing a display device in another exemplary embodiment.
Figure 4:
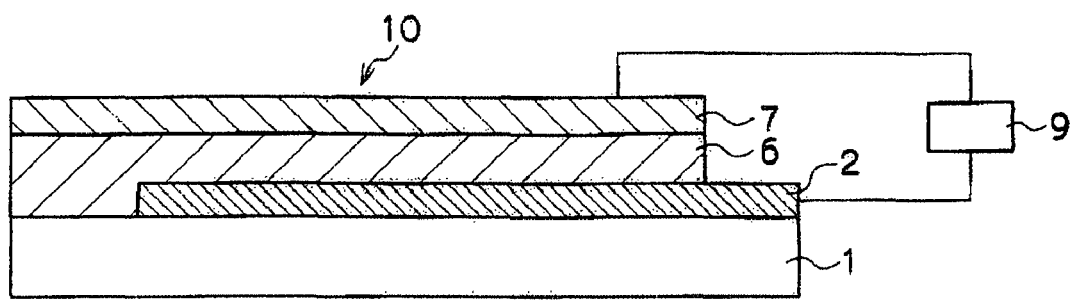
FIG. 4 is a schematic diagram showing a display device in another exemplary embodiment.

A more detailed description is given below with reference to the drawings, but the exemplary embodiment is not limited thereto. FIG. 1, FIG. 2 and FIG. 3 show examples where there are plural organic compound layers, and FIG. 4 shows an example where there is one organic compound layer. In FIG. 1 to FIG. 4, the same reference characters are used for members having the same function.

An organic electroluminescence element 10 shown in FIG. 1 has a transparent electrode 2, a light-emitting layer 4, at least one layer 5 selected from an electron-transporting layer and an electron injection layer, and a back electrode 7, disposed in this order on a transparent insulating substrate 1, and corresponds to the layer structure (1). However, when the layer shown by the reference character 5 consists of an electron-transporting layer and an electron injection layer, the electron-transporting layer, the electron injection layer and the back electrode 7 are layered in this order at the back electrode 7 side of the light-emitting layer 4.

An organic electroluminescence element 10 shown in FIG. 2 has a transparent electrode 2, at least one layer 3 selected from a hole-transporting layer and a hole injection layer, a light-emitting layer 4, at least one layer 5 selected from an electron-transporting layer and an electron injection layer, and a back electrode 7, disposed in this order on a transparent insulating substrate 1, and corresponds to the layer structure (2). However, when the layer shown by the reference character 3 consists of a hole-transporting layer and a hole injection layer, the hole injection layer,the hole-transporting layer and the light-emitting layer 4 are layered in this order at the back electrode 7 side of the transparent electrode 2. When the layer shown by the reference character 5 consists of an electron-transporting layer and an electron injection layer, the electron-transporting layer, the electron injection layer and the back electrode 7 are layered in this order at the back electrode 7 side of the light-emitting layer 4.

An organic electroluminescence element 10 shown in FIG. 3 has a transparent electrode 2, at least one layer 3 selected from a hole-transporting layer and a hole injection layer, a light-emitting layer 4 and a back electrode 7, disposed in this order on a transparent insulating substrate 1, and corresponds to the layer structure (3). However, when the layer shown by the reference character 3 consists of a hole-transporting layer and a hole injection layer, the hole injection layer, the hole-transporting layer and the light-emitting layer 4 are layered in this order at the back electrode 7 side of the transparent electrode 2.

An organic electroluminescence element 10 shown in FIG. 4 has a transparent electrode 2, a light-emitting layer 6 with a charge transporting ability and a back electrode 7, disposed in this order on a transparent insulating substrate 1.

It is possible to adopt, for example, a top emission structure, a transmission structure using transparent electrodes for both of the anode and the cathode, in which case the structure may be a structure in which plural layer structures selected from those shown in FIGS. 1 to 4 are stacked.

Hereinafter, more specific descriptions are given.

In the layer structure of each of the organic electroluminescence elements shown in FIGS. 1 to 4, the transparent insulating substrate 1 may be transparent so as to allow extraction of emitted light, and glass, plastic film etc. may be used. The term "transparent" means that the transmittance of light in the visible region is 10% or more, and the transmittance is preferably 75% or more. The transparent electrode 2, similarly to the transparent insulating substrate, may be transparent so as to allow extraction of emitted light, and may have a large work function so as to allow hole injection; the work function may be 4 eV or more.

Specifically, an oxide film such as indium tin oxide (ITO), tin oxide (NESA), indium oxide, zinc oxide or indium zinc oxide, or deposited or sputtered gold, platinum palladium, or the like may be used. The sheet resistance of the electrode is preferably lower, for example several hundreds Ω/sq or less, and even more preferably 100 Ω/sq or less. Like the transparent insulating substrate, the transmittance of light in the visible region is preferably 10% or more, and the transmittance is more preferably 75% or more.

For the purpose of improving the durability or light emitting efficiency of the organic electroluminescence element, a hole-transporting material for regulating hole mobility that is other than the charge-transporting polyester may be mixed and dispersed in the range of 0.1 to 50% by mass based on the charge-transporting polyester used in the exemplary embodiment. Examples of this hole-transporting material include tetraphenylenediamine derivatives, triphenylamine derivatives, carbazole derivatives, stilbene derivatives, arylhydrazone derivatives, and porphyrin derivatives, among which tetraphenylenediamine derivatives and triphenylamine derivatives are preferable because of their excellent compatibility with the charge-transporting polyester.

Similarly, for regulating electron mobility, the electron-transporting material may be mixed and dispersed in the range of 0.1 to 50% by mass based on the charge-transporting polyester. Examples of this electron-transporting material include oxadiazole derivatives, nitro-substituted fluorenone derivatives, diphenoquinone derivatives, thiopyran dioxide derivatives, silole derivatives, chelate-type organometallic complexes, polynuclear or condensed aromatic ring compounds, perylene derivatives, triazole derivatives, and fluorenylidene methane derivatives.

When it is necessary to control both of the hole mobility and the electron mobility, both of the hole-transporting material and electron-transporting material may be mixed in the charge-transporting polyester.

For improving film-forming properties and for preventing pinholes, suitable resins (polymers) and/or additives may be added. Specific examples of resins include electroconductive resins such as a polycarbonate resin, a polyester resin, a methacrylic resin, an acrylic resin, a polyvinyl chloride resin, a cellulose resin, a urethane resin, an epoxy resin, a polystyrene resin, a polyvinyl acetate resin, a styrene butadiene copolymer, a vinylidene chloride-acrylonitrile copolymer, a vinyl chloride-vinyl acetate-maleic anhydride copolymer, a silicone resin, a poly-N-vinylcarbazole resin, a polysilane resin, a polythiophene, and a polypyrrole. As additives, known antioxidants, UV absorbers and plasticizers may be used.

A hole injection layer and/or an electron injection layer may be used in order to improve charge injection properties. Examples of usable hole injection materials include phenylenediamine derivatives, phthalocyanine derivatives, indanthrene derivatives, and polyalkylene dioxythiophene derivatives. These derivatives may be mixed with a Lewis acid, sulfonic acid etc. Examples of the electron injection material include metals such as Li, Ca and Sr, metal fluorides such as LiF and MgF$_2$, and metal oxides such as MgO, Al$_2$O$_3$ and LiO.

If the charge-transporting polyester is used for other purposes than light emitting function, a light-emitting compound is used as a light-emitting material. As the light-emitting material, a compound showing high light-emitting quantum efficiency in a solid state may be used. The light-emitting material may be either a low-molecular-weight compound or a high-molecular-weight compound. In the case of such organic low-molecular-weight compound, suitable examples thereof include chelate organometallic complexes, polynuclear or condensed aromatic ring compounds, perylene derivatives, coumarin derivatives, styrylarylene derivatives, silole derivatives, oxazole derivatives, oxathiazole derivatives, and oxadiazole derivatives. In the case of the high-molecular-weight compound, suitable examples thereof include polyparaphenylene derivatives, polyparaphenylenevinylene derivatives, polythiophene derivatives and polyacetylene derivatives. Suitable specific examples include, but are not limited to, the following light-emitting materials (IV-1) to (IV-17). In the light-emitting materials (IV-13) to (IV-17), V represents a functional group selected from the groups (7) to (17) shown above for V, and n and j each represent 1 or an integer of 2 or more.

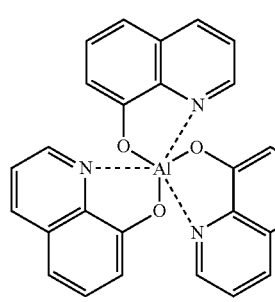
(IV-1)

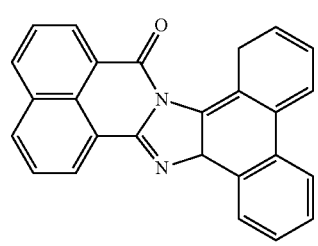
(IV-2)

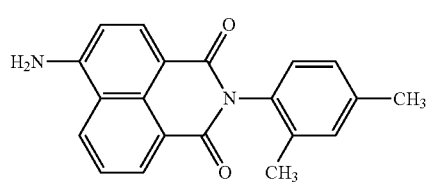
(IV-3)

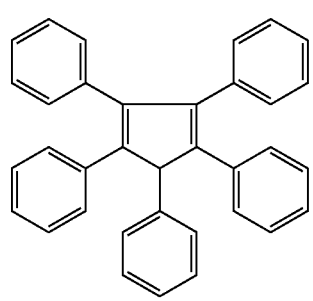
(IV-4)

-continued
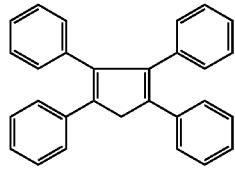
(IV-5)
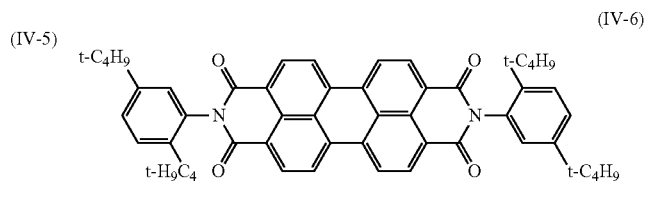
(IV-6)
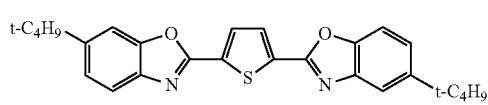
(IV-7)
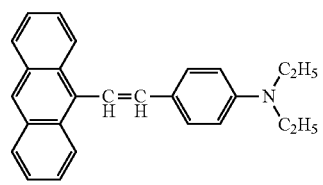
(IV-8)
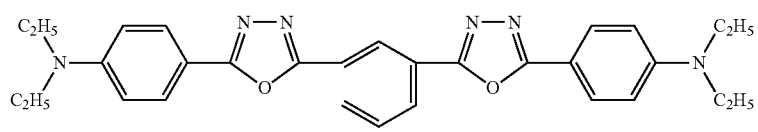
(IV-9)
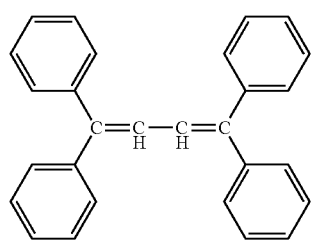
(IV-10)
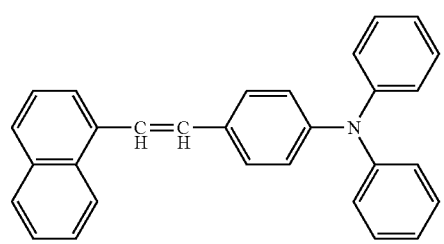
(IV-11)
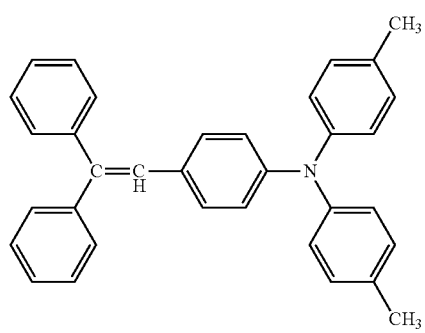
(IV-12)
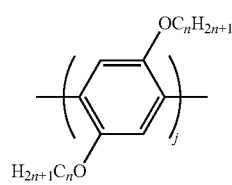
(IV-13)
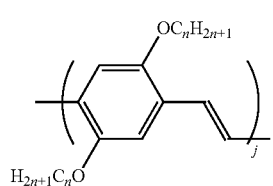
(IV-14)
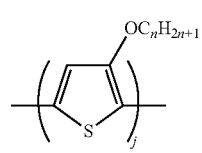
(IV-15)
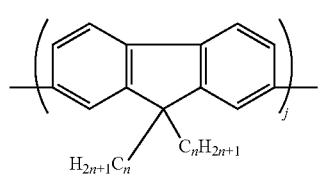
(IV-16)
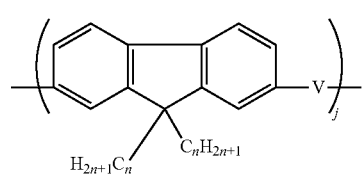
(IV-17)

For the purpose of improving the durability or light emitting efficiency of the element, the light emitting material or the charge-transporting polyester may be doped with a dye compound as a guest material, wherein the dye compound is different from the light-emitting material. The doping ratio of the dye compound in the light-emitting layer may be approximately from 0.001 to 40% by mass, preferably approximately from 0.001 to 10% by mass. The dye compound to be used in such doping may be an organic compound having an excellent compatibility with the light emitting material and the charge-transporting polyester and not preventing formation of an excellent thin film as the light-emitting layer. Suitable examples thereof include coumarin derivatives, DCM derivatives, quinacridone derivatives, rubrene derivatives, porphyrin derivatives, and metal complex compounds of Ir, Eu, Pt etc. Specific examples thereof include, but are not limited to, the following dye compounds (V-1) to (V-6).

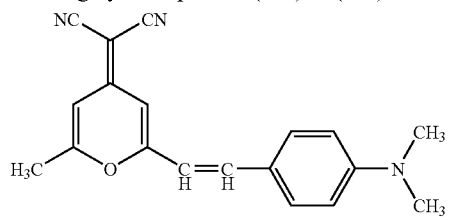

(V-1)

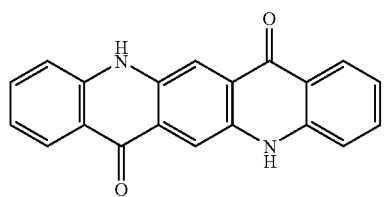

(V-2)

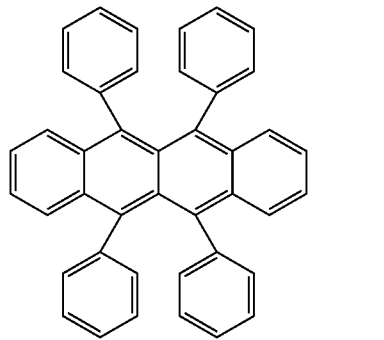

(V-3)

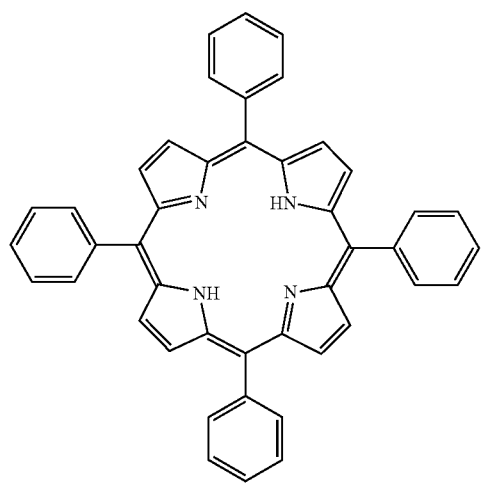

(V-4)

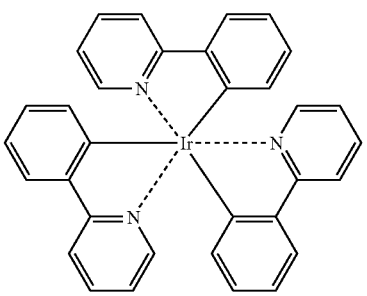

(V-5)

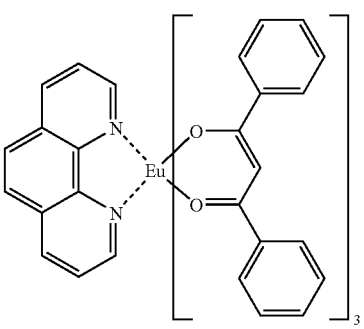

(V-6)

In the case of the layer structure of each of the organic electroluminescence elements shown in FIGS. 1 to 4, those materials that can be vacuum-deposited and have a lower work function for injection of electrons, such as metals, metal oxides and metal fluorides, may be used in the back electrode 7. Examples of the metals include magnesium, aluminum, gold, silver, indium, lithium, calcium, and alloys thereof. Examples of the metal oxides include lithium oxide, magnesium oxide, aluminum oxide, indium tin oxide, tin oxide, indium oxide, zinc oxide, and indium zinc oxide. Examples of the metal fluorides include lithium fluoride, magnesium fluoride, strontium fluoride, calcium fluoride, and aluminum fluoride. A protective layer may be provided on the back electrode 7 in order to prevent deterioration of the organic electroluminescence element due to moisture or oxygen.

Specific examples of the material for the protective layer include metals such as In, Sn, Pb, Au, Cu, Ag, and Al, metal oxides such as MgO, SiO₂, and TiO₂, and resins such as polyethylene resin, polyurea resin, and polyimide resin. Techniques such as a vacuum vapor deposition method, a sputtering method, a plasma polymerization method, a CVD method, and a coating method may be applied for forming the protective layer.

The organic electroluminescence element shown in each of FIGS. 1 to 4 may be formed by successively forming, on a transparent electrode 2, individual layers corresponding to the layer structure of the organic electroluminescence element. At least one layer 3 selected from a hole-transporting layer and a hole injection layer, a light-emitting layer 4, and at least one layer 5 selected from an electron-transporting layer and an electron injection layer, or a light-emitting layer 6 having a charge transporting ability may be formed on the transparent electrode 2 by providing the respective materials by a vacuum vapor deposition method or by a spin coating, casting, dipping or inkjet method using a coating liquid obtained by dissolving or dispersing such materials in a suitable organic solvent. Among the methods above, the inkjet method is preferable because this method allows application of only a required amount of the layer-forming material on the positions of desired pixels, reduces unnecessary consumption of the materials, is thus not harmful to the global environment, allows high-definition patterning and easy applicability to a large panel, provides a greater degree of freedom in the material on which printing is conducted, etc. Specifically, the method for manufacturing the organic electroluminescence element may have a coating step of applying, by an inkjet method, a coating solution containing the constituent component(s) of the organic compound layer dissolved in a solvent.

When the inkjet method is used, an organic compound layer coating solution is used in place of ink, and the organic compound layer coating solution in a droplet form is discharged from a nozzle of a droplet discharge head, thereby forming an organic compound layer of desired thickness and shape on a desired position of a substrate.

The fundamental structure and principle of the droplet discharge head may be the same as those of a recording head used in an inkjet printer. That is, a method of discharging the organic compound layer coating solution in a droplet form (a piezo-ink-jet system using a piezoelectric element, a thermal inkjet system utilizing a heat boiling phenomenon) through a nozzle by applying an exogenous stimulus such as pressure or heat to the organic compound layer coating solution, may be used.

In production of the organic electroluminescence element in the exemplary embodiment, the external stimulus is preferably pressure rather than heat. The reason is as follows. When the external stimulus is heat, the viscosity of the organic compound layer coating solution is significantly changed by heat during the inkjet printing process from the discharge of the organic compound layer coating solution through the nozzle to the formation (solidification) of a coating film through evaporation of the solvent in the organic compound layer coating solution provided on a substrate; therefore, it is sometimes difficult to control the leveling properties and the patterning accuracy. In addition, charge-transporting polyesters inferior in heat resistance cannot be utilized, thus limiting the freedom in the selection of materials.

An apparatus used in production of the organic electroluminescence element in the exemplary embodiment utilizing the inkjet method may have, in addition to the droplet discharge head, additional devices, such as a fixing device that fixes the substrate on which the organic electroluminescence element is to be formed, a conveying device that conveys the substrate, and a droplet discharge head scanning device that moves the droplet discharge head in the plane direction of a substrate in a scanning manner, in accordance with necessity.

The composition and physical properties of the organic compound layer coating solution are not particularly limited, but the viscosity of the organic compound layer coating solution is preferably in the range of 0.01 to 1000 cps (more preferably 1 to 100 cps) at 25° C.

When the viscosity is less than 0.01. cps, the organic compound layer coating solution applied onto a substrate spreads easily in the plane direction of the substrate, and thus there are cases where the regulation of coating thickness is difficult and patterning accuracy is deteriorated. When the viscosity is higher than 1000 cps, the viscosity of the organic compound layer coating solution is so high that discharging errors easily occur in some cases.

The viscosity of the organic compound layer coating solution may be adjusted to a desired value by regulating the content of the charge-transporting polyester, the contents of other optional additive components that are added as necessary, the molecular weight of the charge-transporting polyester, and the like.

The thicknesses of at least one layer 3 selected from the hole-transporting layer and the hole injection layer, the light-emitting layer 4, at least one layer 5 selected from the electron-transporting layer and the electron injection layer, and the light-emitting layer 6 having a charge-transporting ability, are each preferably in the range of 10 μm or less, more preferably 0.001 to 5 μm. The dispersed state of each of the above materials (the non-conjugated polymer, the light-emitting material etc.) may be a molecular dispersion state or a particulate state such as fine crystals. The dispersion solvent used in the film-forming method using a coating solution should be selected in consideration of the dispersibility and solubility of the respective materials so as to realize the molecular dispersion state. A ball mill, a sand mill, a paint shaker, an attriter, a homogenizer, ultrasonic wave or the like may be used for dispersing the materials into a particulate state.

In the case of an organic electroluminescence element shown in FIG. 1 or 2, the organic electroluminescence element in the exemplary embodiment is obtained by forming the back electrode 7 on at least one layer 5 selected from the electron-transporting layer and the electron injection layer by a method such as vacuum deposition or sputtering.

In the case of an organic electroluminescence element shown in FIG. 3, the organic electroluminescence element in the exemplary embodiment is obtained by forming the back electrode 7, for example by vacuum deposition or sputtering, on the light-emitting layer 4 or on the light-emitting layer 6 having a charge-transporting ability.

The organic electroluminescence element in the exemplary embodiment may be used for example in a display, an electronic paper, a backlight, an illumination source, an electrophotographic exposure device, a sign and a signboard.

In the following, the display device in the exemplary embodiment is described in detail.

The display device in the exemplary embodiment has the above-described organic electroluminescence element in the exemplary embodiment and a driving unit that drives the organic electroluminescence element.

As shown in FIGS. 1 to 4, a specific example of the display device is a device including a voltage applying device 9 as a driving unit that are connected to the pair of electrodes (electrode 2 and back electrode 7) of the organic electroluminescence element and applies a DC voltage between the pair of electrodes.

With respect to the method of driving the organic electroluminescence element using the voltage applying device 9, the organic electroluminescence element may be allowed to emit light by, for example, applying a DC voltage of 4V to 20 V between the pair of electrodes at a current density of 1 mA/cm$^2$ to 200 mA/cm$^2$.

In the above description, the organic electroluminescence element in the exemplary embodiment is described by reference to the minimum unit (one pixel unit). However, the organic electroluminescence element may be applied to a display device in which plural pixel units (organic electroluminescence elements) are arranged in at least one of a matrix and a segment shape. When arranging the organic electroluminescence elements in a matrix shape, the electrodes only may be disposed in the matrix shape, or the one or more organic compound layers, as well as the electrodes, may be disposed in the matrix shape. When arranging the organic electroluminescence elements in a segment shape in the exemplary embodiment, electrodes only may be disposed in the segment shape, or the one or more organic compound layers, as well as, the electrodes may be disposed in the segment shape. The organic one or more compound layers disposed in the matrix or segment shape may be prepared easily by the inkjet method described above.

As the method of driving the display device, techniques conventionally known in the art may be used, such as simple matrix driving in which plural row electrodes and plural column electrodes are disposed and the row electrodes are scan-driven while the column electrodes are driven together according to the image information corresponding to each row electrode, or active matrix driving with pixel electrodes arranged for the respective pixels.

EXAMPLES

Hereinafter, the present invention will be described in more detail by reference to the Examples. However, these examples are not intended to limit the scope of the invention.

Example 1

Synthesis Example 1

Acetanilide (25.0 g), methyl 4-iodophenylpropionate (64.4 g), potassium carbonate (38.3 g), copper sulfate pentahydrate (2.3 g), and n-tridecane (50 ml) are introduced into a 500-ml three-necked flask, and are heated under stirring in a nitrogen stream at 230° C. for 20 hours. After the reaction is finished, a solution of potassium hydroxide (15.6 g) in ethylene glycol (300 ml) is added thereto, the mixture is heated under reflux in a nitrogen stream for 3.5 hours and then cooled to room temperature (25° C). The reaction solution is poured into 1 L of distilled water and neutralized with hydrochloric acid, to give a crystalline precipitate. The crystal is collected by filtration under suction, washed with water, and transferred into a 1-L flask. Toluene (500 ml) is added thereto, then the mixture is heated under reflux while water is removed by azeotropy. A solution of conc. sulfuric acid (1.5 ml) in methanol (300 ml) is added thereto, followed by heating under reflux in a nitrogen stream for 5 hours. After the reaction is finished, the product is extracted with toluene, and the organic layer is washed with distilled water. Then, the organic layer is dried over sodium sulfate anhydride and the solvent is removed under reduced pressure, and recrystallization from hexane gives 36.5 g of DAA-1.

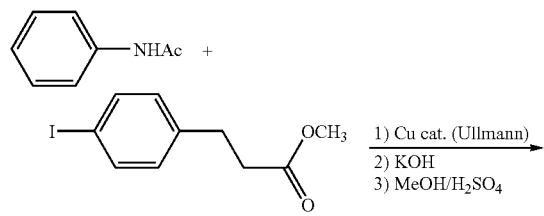

1) Cu cat. (Ullmann)
2) KOH
3) MeOH/H$_2$SO$_4$

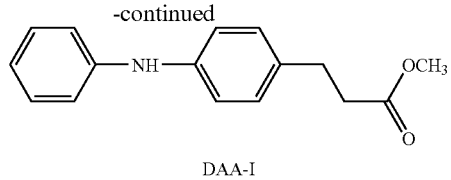

DAA-1

1,2-Phenylene diamine (2.9 g) and 4.4'-dibromobenzil (10 g) are then introduced into a 500-ml three-necked flask equipped with a thermometer, a condenser and a magnetic stirrer, and then dissolved in 200 ml of isopropyl ether. The mixture is heated under reflux for 1 hour under stirring with the magnetic stirrer. After the disappearance of the spot of 1,2-phenylene diamine is confirmed by TLC (hexane/ethyl acetate=3/1), the reaction mixture is cooled to room temperature (25° C.). Crystals precipitated during the reaction, and are collected by filtration under suction. The crystals are washed with 50 ml of methanol and then vacuum-dried at 70° C. for 15 hours to give a quinoxaline dihalogen derivative [Intermediate 1A] (10 g).

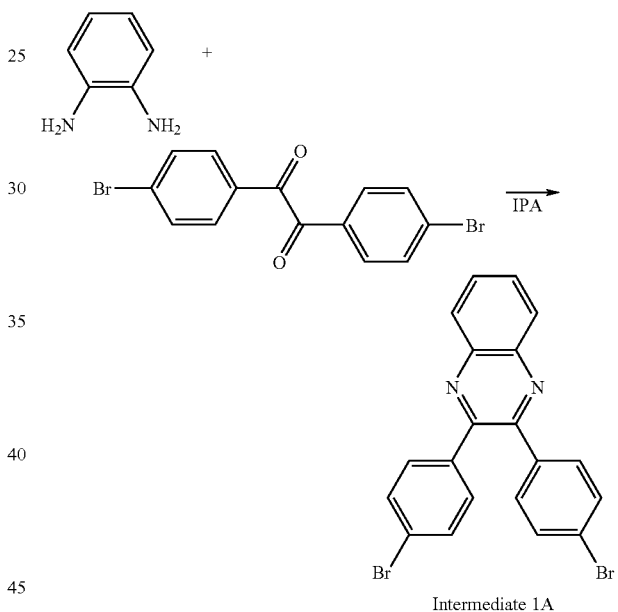

Intermediate 1A

Then, DAA-1 (8.0 g), Intermediate 1A (6.3 g), palladium (II) acetate (150 mg), and rubidium carbonate (19.6 g) are introduced into a 200-ml three-necked flask equipped with a thermometer, a condenser and a magnetic stirrer, and then dissolved in 50 ml of xylene. Tri(tertiary-butyl)phosphine (420 mg) is quickly added thereto, and the mixture is heated under reflux for 9 hours under stirring with the magnetic stirrer in a nitrogen atmosphere. After the disappearance of the spot of Intermediate 1A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (100 ml), water (200 ml×3) and saturated saline (200 ml×1) in this order until the mixture becomes neutral. The reaction mixture is dried over sodium sulfate anhydride, purified by silica gel column chromatography (hexane/ethyl acetate=3/1) and then vacuum-dried at 70° C. for 15 hours to give Intermediate 1B (5.2 g) in a yield of 46%. The melting point of Intermediate 1B is the range from 135 to 136° C.

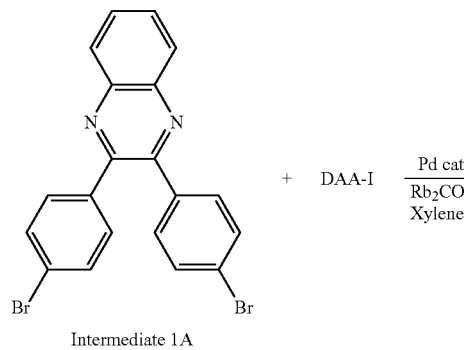

Intermediate 1A

+ DAA-I $\xrightarrow[\text{Xylene}]{\text{Pd cat} \atop \text{Rb}_2\text{CO}_3}$

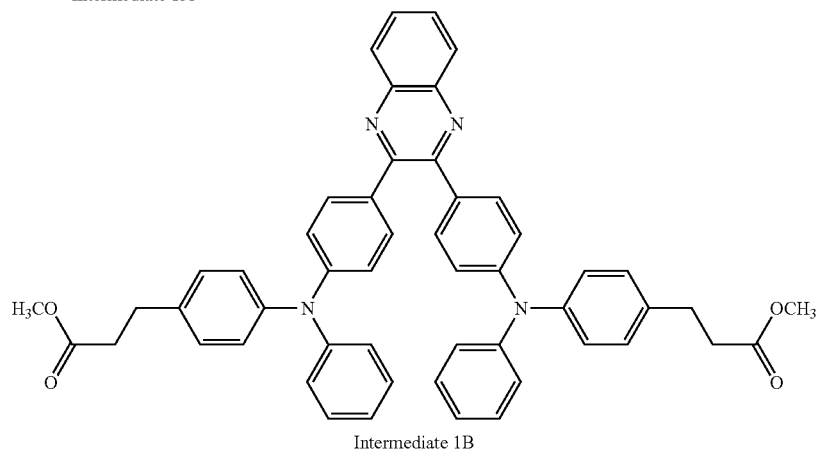

Intermediate 1B

Then, 1.5 g of intermediate 1B, 10 ml of ethylene glycol and 0.02 g of tetrabutoxytitanium are introduced into a 50-ml three-necked eggplant-shaped flask, and the mixture is heated at 200° C. for 5 hours under stirring in a nitrogen atmosphere. After the disappearance of the starting material 1 is confirmed by TLC, the mixture is heated to 210° C. at a reduced pressure of 50 Pa and allowed to react for 6 hours during which the ethylene glycol is distilled away. The mixture is then cooled to room temperature (25° C.) and dissolved in 50 ml of tetrahydrofuran, and the insoluble matter is filtered out by filtration through a 0.5-μm polytetrafluoroethylene (PTFE) filter. The solvent is removed from the filtrate under reduced pressure, and then the residue is dissolved in 300 ml of monochlorobenzene and washed with 1 N HCl (300 ml) and water (500 ml×3) in this order. The monochlorobenzene solution is evaporated to a volume of 30 ml under reduced pressure and added dropwise into 800 ml of a mixture of ethyl acetate/methanol (1/3), to re-precipitate a polymer. The polymer thus obtained is filtered out, washed with methanol, and vacuum-dried at 60° C. for 16 hours, to give 0.9 g of a polymer [exemplary compound (1)]. Analysis of the molecular weight of this polymer by gel-permeation chromatography (GPC) (HLC-8120GPC manufactured by Tosoh Corporation) shows an MW of $6.1 \times 10^4$ (styrene-equivalent molecular weight) and an MW/Mn of 1.01, and the polymerization degree p as determined from the monomer molecular weight is 76.

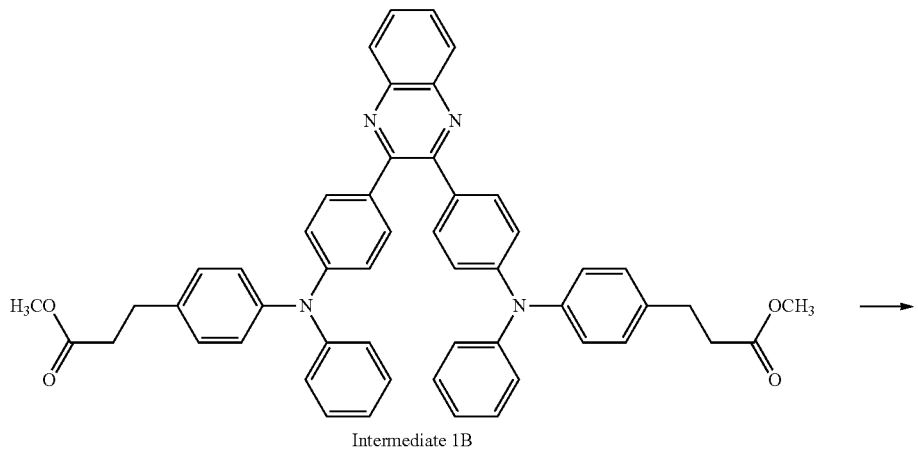

Intermediate 1B

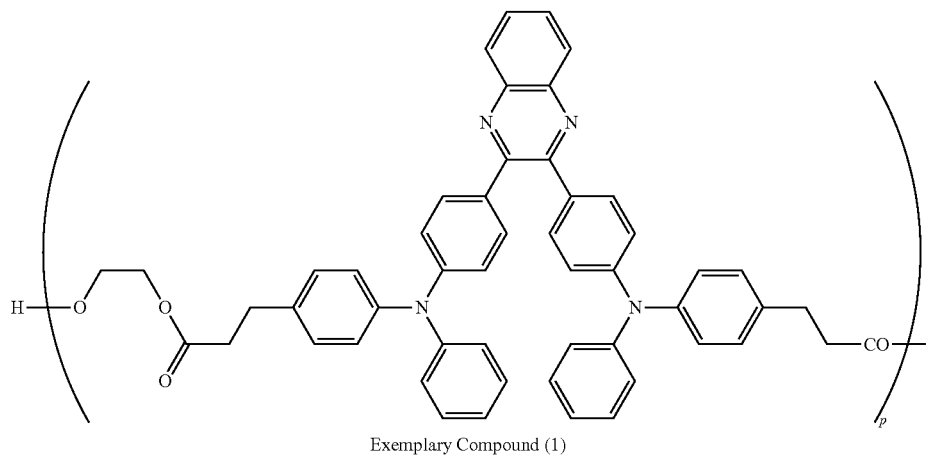

Exemplary Compound (1)

Preparation of an Element

ITO (manufactured by Sanyoshinku Co., Ltd.) formed on a transparent insulating substrate is patterned by photolithography with a strip-shaped photomask and then etched thereby forming an strip-shaped ITO electrode (width 2 mm). Then, this ITO glass substrate is ultrasonicated sequentially in a neutral detergent solution, ultrapure water, acetone (for electronic industry, manufactured by Kanto Kagaku), and isopropanol (for electronic industry, manufactured by Kanto Kagaku) in this order for 5 minutes each, whereby the glass substrate is cleaned, followed by drying with a spin coater. A 5 wt % solution of the charge-transporting polyester [exemplary compound (1)] in monochlorobenzene is prepared, filtered though a 0.1-μm PTFE filter and applied onto the substrate by dipping to form a thin film having a thickness of 0.050 μm as a hole-transporting layer. The exemplary compound (IV-1) is vapor-deposited as a light emitting material to form a light-emitting layer of 0.055 μm in thickness. A metallic mask provided with strip-shaped holes is arranged, and an Mg—Ag alloy is co-deposited thereon to form a back electrode having a width of 2 mm and a thickness of 0.15 μm such that the back electrode intersects with the ITO electrode. The effective area of the organic electroluminescence element formed is 0.04 cm$^2$.

Example 2

Synthesis Example 2

4-Phenylacetanilide (4.0 g), methyl 4-iodophenylpropionate (6.4 g), potassium carbonate (3.9 g) and copper sulfate pentahydrate (0.40 g) are introduced into a 100-ml three-necked flask equipped with a thermometer, a condenser and a magnetic stirrer, and then dissolved in o-dichlorobenzene (20 ml). The mixture is heated under stirring in a nitrogen atmosphere at 185° C. for 13 hours. After the reaction is finished, a solution of potassium hydroxide (1.3 g) in ethylene glycol (25 ml) is added thereto, and the mixture is heated under reflux in a nitrogen atmosphere for 5 hours. After the reaction is finished, the reaction mixture is cooled to room temperature (25° C.), then poured into water (200 ml) and neutralized with hydrochloric acid, to give a crystalline precipitate. The crystal is collected by filtration, washed with water and transferred to a 1-L flask. Toluene (300 ml) is added thereto, the mixture is heated under reflux while water is removed by azeotropy, a solution of conc. sulfuric acid (0.5 ml) in methanol (100 ml) is added, and the mixture is heated under reflux in a nitrogen stream for 3 hours. After the reaction is finished, the reaction mixture is poured into distilled water and extracted with toluene. The toluene layer is washed with distilled water and then dried over sodium sulfate anhydride, the solvent is removed under reduced pressure, and recrystallization from a mixture of ethyl acetate/hexane gives 3.2 g of DAA-2.

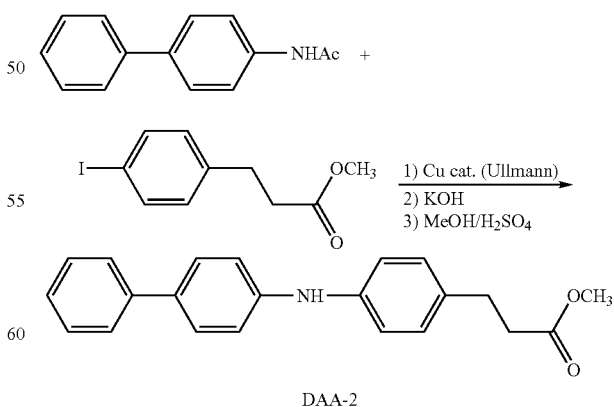

DAA-2

Then, DAA-2 (2.1 g), Intermediate 1A (1.4 g), palladium (II) acetate (36 mg), and rubidium carbonate (4.4 g) are introduced into a 200-ml three-necked flask equipped with a thermometer, a condenser and a magnetic stirrer, and then dissolved in 30 ml of xylene. Tri(tertiary-butyl)phosphine (97 mg) is quickly added thereto, and the mixture is heated under reflux for 5 hours under stirring with the magnetic stirrer in a nitrogen atmosphere. After the disappearance of the spot of Intermediate 1A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (20 ml), water (50 ml×3) and saturated saline (50 ml×1) in this order until the mixture becomes neutral. The reaction mixture is dried over sodium sulfate anhydride, purified by silica gel column chromatography (hexane/ethyl acetate=3/1), washed with 100 ml of a boiling mixture of acetone/methanol, and vacuum-dried at 70° C. for 15 hours to give Intermediate 2A (0.5 g) in a yield of 17%. The melting point of Intermediate 2A is in the range from 177 to 178° C.

appearance of the starting material is confirmed by TLC, the mixture is heated to 210° C. at a reduced pressure of 50 Pa and allowed to react for 6 hours during which the ethylene glycol is distilled away. The mixture is then cooled to room temperature (25° C.) and dissolved in 50 ml of tetrahydrofuran, and the insoluble matter is filtered out by filtration through a 0.5-μl polytetrafluoroethylene (PTFE) filter. The solvent is removed from the filtrate under reduced pressure, then the residue is dissolved in 300 ml of monochlorobenzene and washed with 1 N HCl (300 ml) and water (500 ml×3) in this order. The monochlorobenzene solution is evaporated to a volume of 30 ml under reduced pressure and added dropwise into 800 ml of a mixture of ethyl acetate/methanol (1/3), to re-precipitate a polymer. The polymer thus obtained is filtered out, washed with methanol, and vacuum-dried at 60° C. for 16 hours, to give 0.9 g of a polymer [exemplary compound (9)]. Analysis of the molecular weight of this exemplary compound (9) by gel-permeation chromatography (GPC) shows an MW of $1.0 \times 10^5$ (styrene-equivalent molecular weight) and an MW/Mn of 1.3, and the polymerization degree p as determined from the monomer molecular weight is 86.

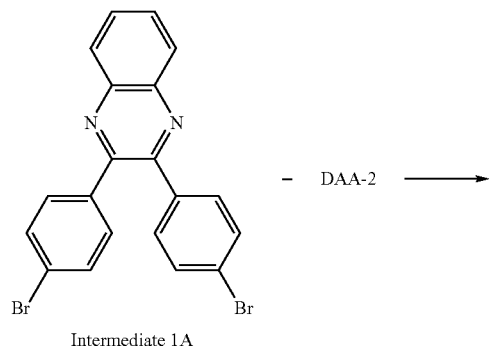

Intermediate 1A

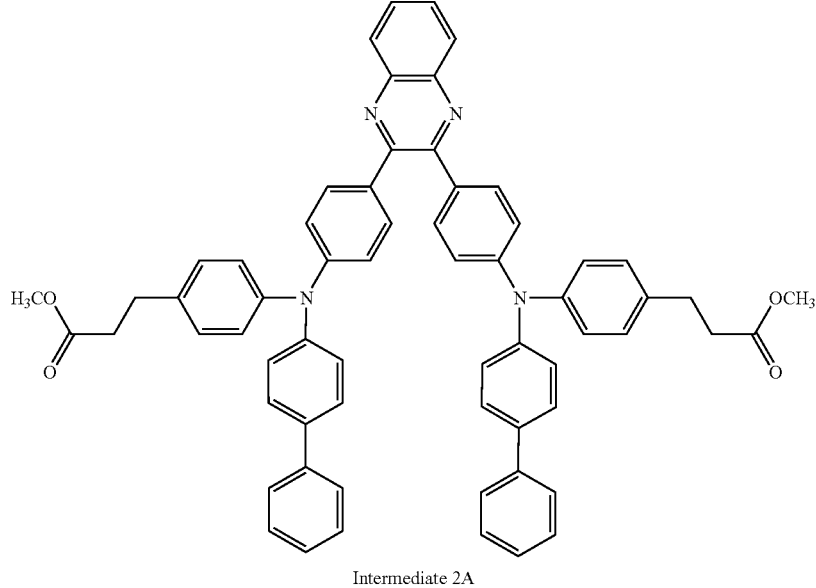

Intermediate 2A 1.2 g of Intermediate 2A, 10 ml of ethylene glycol and 0.02 g of tetrabutoxytitanium are introduced into a 50-ml three-necked eggplant-shaped flask and heated at 200° C. for 7 hours under stirring in a nitrogen atmosphere. After the dis-

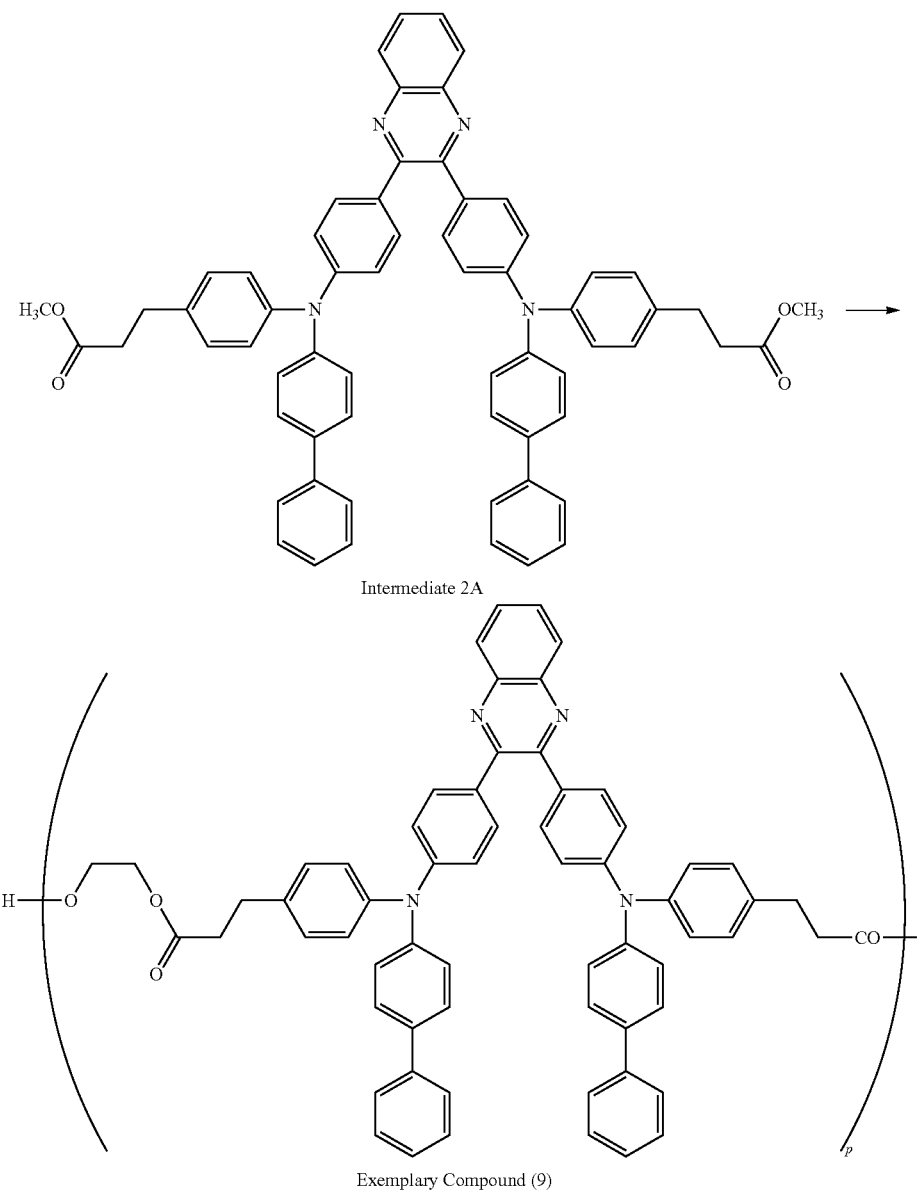

Intermediate 2A

Exemplary Compound (9)

Preparation of an Element

A dichloroethane solution containing 1 part by weight of the charge-transporting polyester [exemplary compound (9)], 4 parts by weight of poly(N-vinylcarbazole) and 10% by weight of the exemplary compound (IV-1) is filtered through a 0.1-μm PTFE filter. An ITO glass substrate etched and cleaned in the same manner as in Example 1 to form a strip-shaped ITO electrode of 2 mm in width is coated by spin coating with the above solution to form a light-emitting layer of 0.15 μm n thickness having a charge transporting ability. After sufficient drying, an Mg—Ag alloy is co-deposited thereon to form a back electrode having a width of 2 mm and a thickness of 0.15 μm such that the back electrode intersects with the ITO electrode. The effective area of the organic electroluminescence element formed is 0.04 cm$^2$.

Example 3

Synthesis Example 3

N-(4-iodophenyl) pyrrole (16 g), methyl 3-(4-acetamidophenyl)propionate (14 g), potassium carbonate (8.3 g), and copper sulfate pentahydrate (1.3 g) are introduced into a 300-ml three-necked flask equipped with a thermometer, a condenser and a magnetic stirrer, and then dissolved in o-dichlorobenzene (50 ml). The mixture is heated under stirring in a nitrogen atmosphere at 180° C. for 24 hours. After the reaction is finished, a solution of potassium hydroxide (4.5 g) in ethylene glycol (100 ml) is added thereto, the mixture is heated under reflux in a nitrogen atmosphere for 4 hours. After the reaction, the reaction mixture is cooled to room temperature (25° C.), then poured into water (300 ml) and neutralized with hydrochloric acid, to give a crystalline precipitate. The crystal is collected by filtration, washed with water, and transferred to a 1-L flask. Toluene (300 ml) is added thereto, the mixture is heated under reflux while water is removed by azeotropy, then methanol (400 ml) and p-toluenesulfonic acid (1.0 g) are added, and the mixture is heated under reflux in a nitrogen stream for 4 hours. After the reaction is finished, the reaction mixture is poured into 1.0 L of distilled water and extracted with toluene. The toluene layer is washed with distilled water, and after drying over sodium sulfate anhydride, the solvent is removed under reduced pressure, and the resulting residue is treated with 10 g of activated earth, and recrystallization from a toluene/hexane mixture gives 13 g of DAA-3.

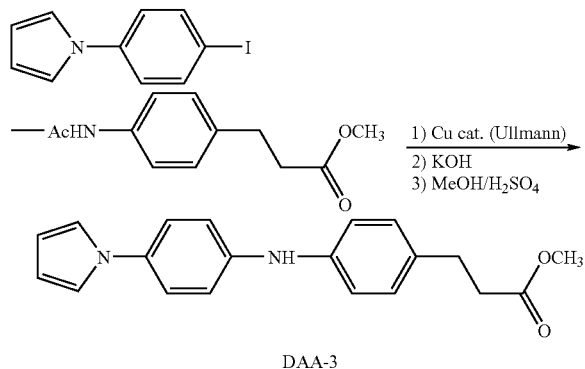

DAA-3

Then, DAA-3 (1.4 g), Intermediate 1A (0.9 g), palladium (II) acetate (22 mg), and rubidium carbonate (2.8 g) are introduced into a 100-ml three-necked flask equipped with a thermometer, a condenser and a magnetic stirrer, and then dissolved in 50 ml of xylene. Tri(tertiary-butyl)phosphine (100 mg) is quickly added thereto, and the mixture is heated under reflux for 8 hours under stirring with the magnetic stirrer in a nitrogen atmosphere. After the disappearance of the spot of Intermediate 1A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (20 ml), water (50 ml×3) and saturated saline (50 ml×1) in this order until the mixture becomes neutral. After drying over sodium sulfate anhydride, the solvent is removed under reduced pressure, and the residue is treated with 2.0 g of activated earth thereby removing colored impurities, then washed with 100 ml of methanol and vacuum-dried at 70° C. for 15 hours to give Intermediate 3A (1.2 g) in a yield of 65%.

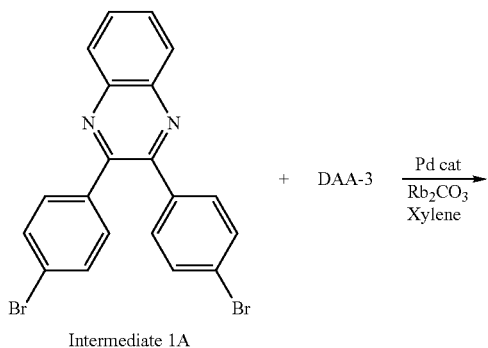

Intermediate 1A

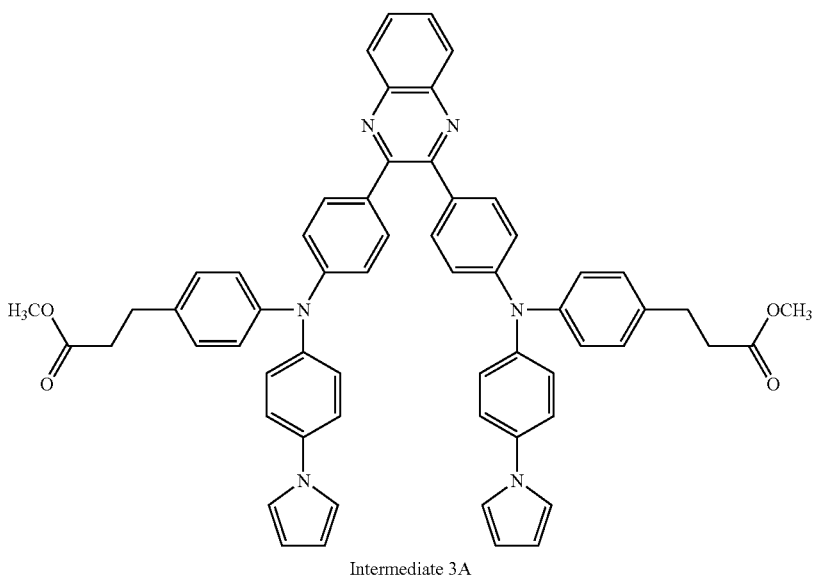

Intermediate 3A 1.2 g of Intermediate 3A is introduced into a 50-ml three-necked eggplant-shaped flask, and a tetrabutyl orthotitanate monomer (10 mg) in ethylene glycol (10 ml) is added thereto in a nitrogen atmosphere, and after degassing, the mixture is allowed to react at 200° C. for 5 hours. Thereafter, the mixture is heated and allowed to react at 230° C. at a reduced pressure of 40 Pa for 5 hours. The mixture is then cooled to room temperature (25° C.) and dissolved in 50 ml of monochlorobenzene under heating, and the insoluble matter is filtered out by filtration through a 0.5-μm PTFE filter under pressure, and the filtrate is added dropwise to 700 ml of a mixture of ethyl acetate/methanol under stirring, to re-precipitate a polymer. The polymer thus obtained is collected by filtration under suction, then washed with 500 ml of methanol and dried to give 0.9 g of a polymer [exemplary compound (33)]. Analysis of the molecular weight of the exemplary compound (33) by gel-permeation chromatography (GPC) shows an MW of $5.4 \times 10^4$ (styrene-equivalent molecular weight) and an MW/Mn of 1.8, and the polymerization degree p as determined from the monomer molecular weight is 59.

Preparation of an Element

On an ITO glass substrate etched and cleaned in the same manner as in Example 1, a charge-transporting polyester [exemplary compound (33)] of 0.050 μm in thickness is formed as a hole-transporting layer in a similar manner to Example 1. The exemplary compound (IV-1) and the exemplary compound (V-1) are formed as a light-emitting layer of 0.065 μm in thickness and the exemplary compound (IV-9) is formed as an electron-transporting layer of 0.030 μm in thickness. Subsequently, an Mg—Ag alloy is co-deposited thereon to form a back electrode having a width of 2 mm and a thickness of 0.15 μm such that the back electrode intersects with the ITO electrode. The effective area of the organic electroluminescence element formed is 0.04 cm$^2$.

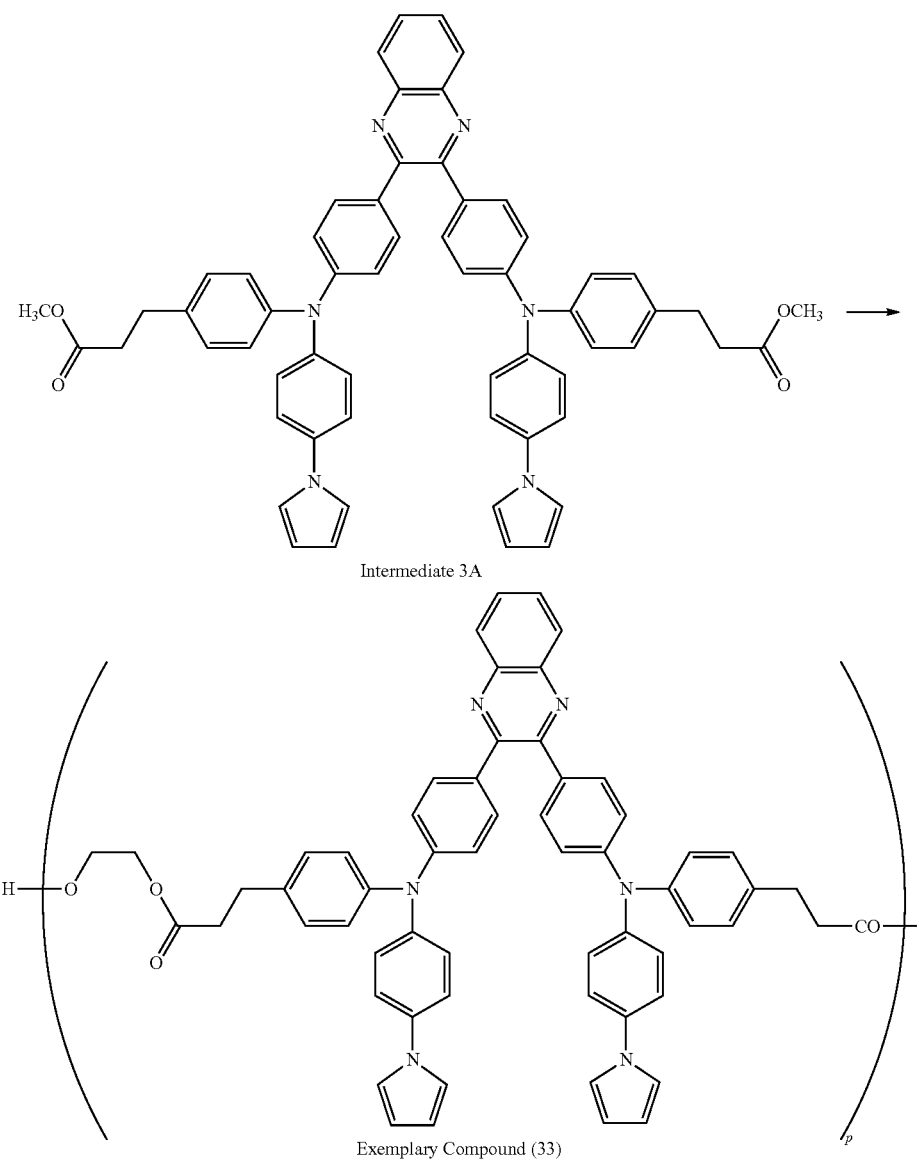

Intermediate 3A

Exemplary Compound (33)

Example 4

Synthesis Example 4

3,4-Diaminotoluene (3.3 g) and 4.4'-dibromobenzil (10 g) are introduced into a 500-ml three-necked flask equipped with a thermometer, a condenser and a magnetic stirrer, and then dissolved in 200 ml of isopropyl ether. The mixture is heated under reflux for 1 hour under stirring with the magnetic stirrer. After the disappearance of the spot of 3,4-diaminotoluene is confirmed by TLC (hexane/ethyl acetate=3/1), the reaction mixture is cooled to room temperature (25° C.). Crystals precipitated during the reaction, and are collected by filtration under suction. The crystals are washed with 50 ml of methanol and then vacuum-dried at 70° C. for 15 hours to give Intermediate 4A (8.5 g).

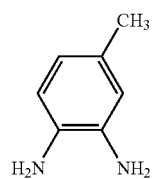

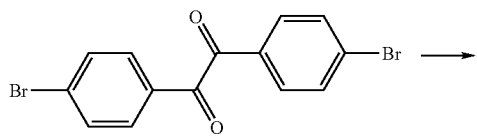

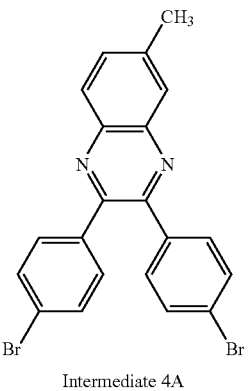

Intermediate 4A

Then, DAA-2 (6.7 g), Intermediate 4A (4.5 g), palladium (II) acetate (110 mg), and rubidium carbonate (14 g) are introduced into a 500-ml three-necked flask equipped with a thermometer, a condenser and a magnetic stirrer, and then dissolved in 200 ml of xylene. Tri(tertiary-butyl)phosphine (800 mg) is quickly added thereto, and the mixture is heated under reflux for 9 hours under stirring with the magnetic stirrer in a nitrogen atmosphere. After the disappearance of the spot of Intermediate 4A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (100 ml), water (200 ml×3) and saturated saline (200 ml×1) in this order until the mixture becomes neutral. The reaction mixture is dried over sodium sulfate anhydride, purified by silica gel column chromatography (hexane/ethyl acetate=3/1) and then vacuum-dried at 70° C. for 15 hours to give Intermediate 4B (2.9 g) in a yield of 65%.

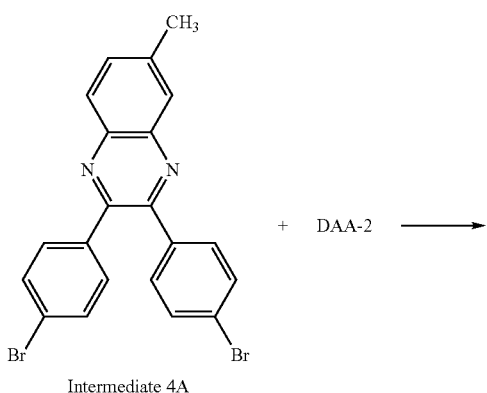

Intermediate 4A

-continued

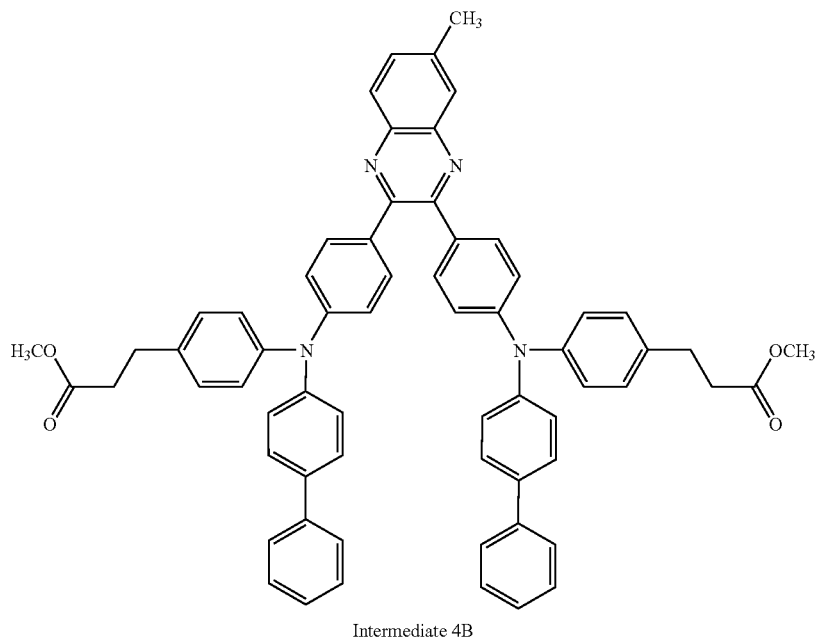
Intermediate 4B 1.2 g of Intermediate 4B is introduced into a 50-ml three-necked eggplant-shaped flask, and a tetrabutyl orthotitanate monomer (10 mg) in ethylene glycol (10 ml) is added thereto in a nitrogen atmosphere, and after degassing, the mixture is allowed to react at 200° C. for 6 hours. Thereafter, the mixture is heated to 230° C. at a reduced pressure of 56 Pa and allowed to react for 7 hours. The mixture is then cooled to room temperature (25° C.) and dissolved in 50 ml of monochlorobenzene under heating, and the insoluble matter is filtered out by filtration through a 0.5-μm PTFE filter under pressure, and the filtrate is added dropwise to 800 ml of a mixture of ethyl acetate/methanol under stirring, to re-precipitate a polymer. The polymer thus obtained is collected by filtration under suction, then washed with 500 ml of methanol, and dried to give 1.0 g of a polymer [exemplary compound (17)]. Analysis of the molecular weight of the exemplar compound (17) by gel-permeation chromatography (GPC) shows an MW of $7.6 \times 10^4$ (styrene-equivalent molecular weight) and an MW/Mn of 1.5, and the polymerization degree p as determined from the monomer molecular weight is 80.

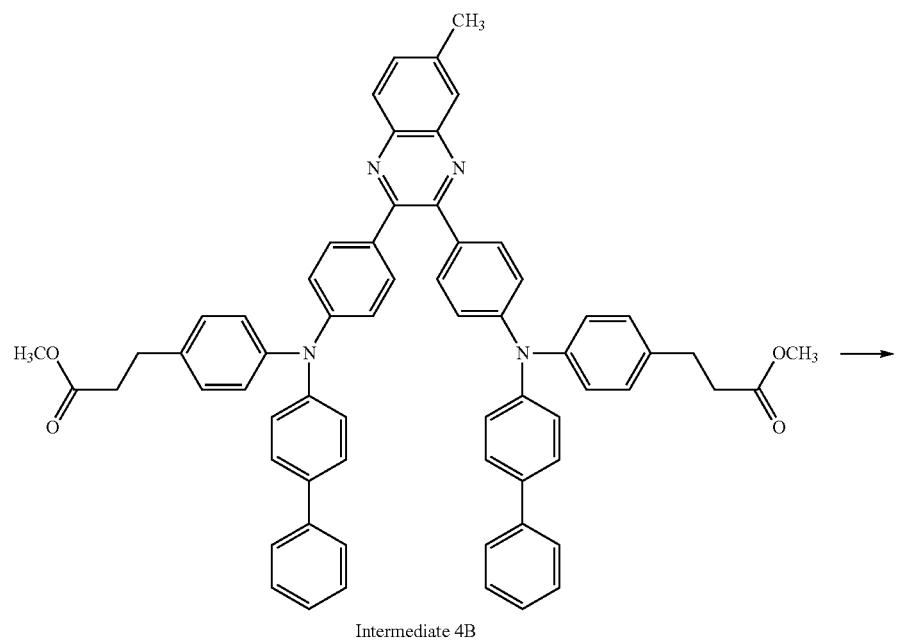
Intermediate 4B

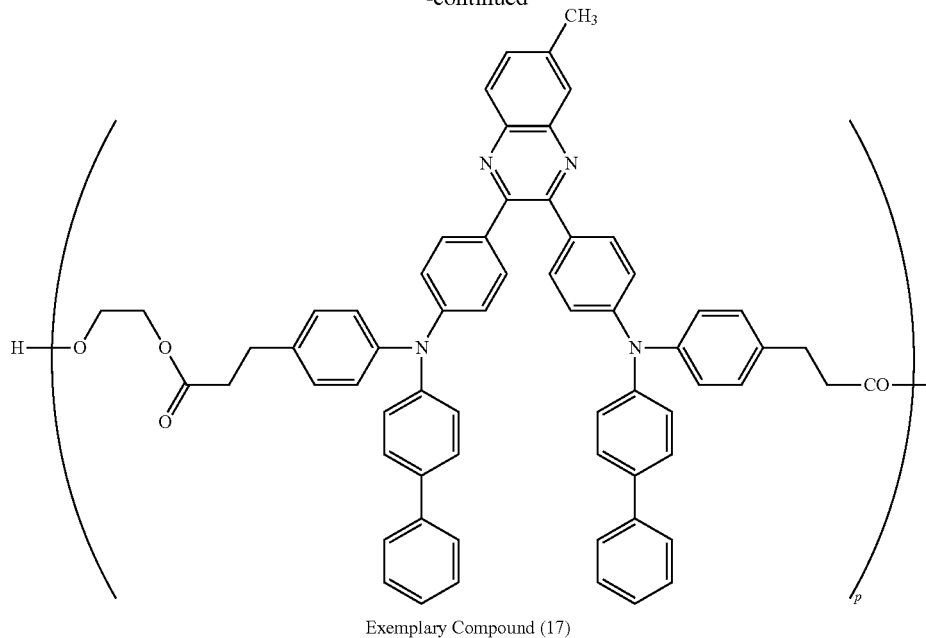

Exemplary Compound (17)

Preparation of an Element

On an ITO glass substrate etched and cleaned in the same manner as in Example 1, a charge-transporting polyester [exemplary compound (17)] of 0.050 μm in thickness is formed as a hole-transporting layer by the inkjet method in a similar manner to Example 1. The exemplary compound (IV-17) and the exemplary compound (V-5) are formed as a light-emitting layer of 0.065 μm in thickness by spin coating. After sufficient drying, Ca and Al are deposited thereon in thicknesses of 0.08 μm and 0.15 μm, respectively, to form a back electrode having a width of 2 mm and a total thickness of 0.23 μm such that the back electrode intersects with the ITO electrode. The effective area of the organic electroluminescence element formed is 0.04 cm².

Example 5

Synthesis Example 5

2.9 g of triphenylphosphine palladium (0), 7.0 g of 4-chloro-1,2-phenylenediamine, 50 ml of 2 M sodium bicarbonate aqueous solution, and 6.1 g phenylboric acid are introduced into a 300-ml three-necked flask in a nitrogen atmosphere, and dissolved in 100 ml of toluene. After stirring under reflux for 5 hours, the completion of the reaction is confirmed by TLC. Thereafter, the reaction mixture is washed with water until the mixture becomes neutral, and then dried over sodium sulfate. The solvent is distilled away under reduced pressure, and recrystallization from ethanol gives 4.6 g of a diamino derivative.

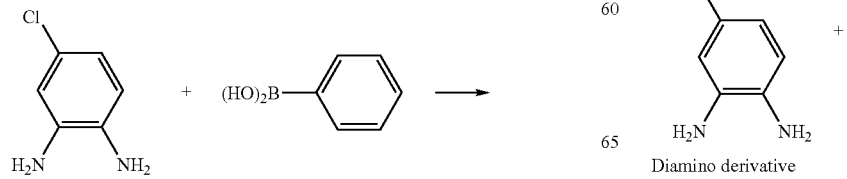

-continued

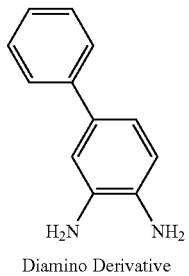

Diamino Derivative

The diamino derivative (3.6 g) and 4.4'-dibromobenzil (7.8 g) are then introduced into a 500-ml three-necked flask equipped with a thermometer, a condenser and a magnetic stirrer, and then dissolved in 200 ml of isopropyl ether. The mixture is heated under reflux for 1 hour under stirring with the magnetic stirrer. After the disappearance of the spot of 1,2-phenylenediamine is confirmed by TLC (hexane/ethyl acetate=3/1), the reaction product is cooled to room temperature (25° C.). Crystals precipitated during the reaction, and are collected by filtration under suction. The crystals are washed with 100 ml of methanol and then vacuum-dried at 70° C. for 15 hours to give Intermediate 5A (8.0 g).

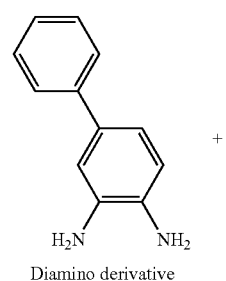

Diamino derivative

-continued

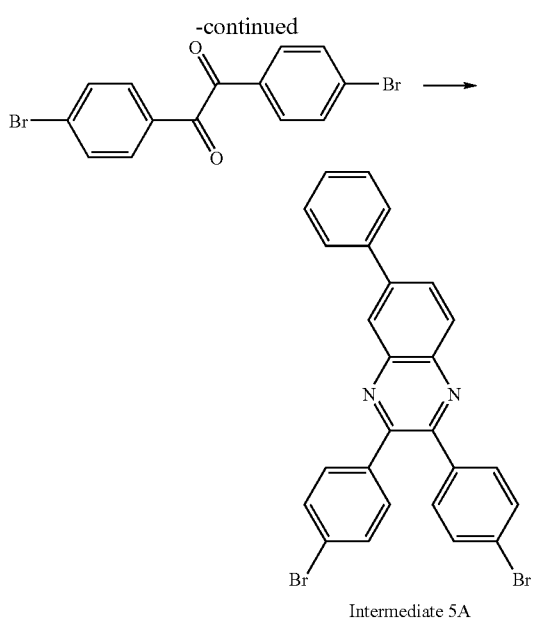
Intermediate 5A

Then, DAA-2 (6.7 g), Intermediate 5A (5.1 g), palladium (II) acetate (110 mg), and rubidium carbonate (14 g) are introduced into a 300-ml three-necked flask equipped with a thermometer, a condenser and a magnetic stirrer, and then dissolved in 200 ml of xylene. Tri(tertiary-butyl)phosphine (800 mg) is quickly added thereto, and the mixture is heated under reflux for 12 hours under stirring with the magnetic stirrer in a nitrogen atmosphere. After the disappearance of the spot of Intermediate 5A is confirmed by TLC (hexane/ethyl acetate=3/1), the reaction mixture is cooled to room temperature (25° C.). After inorganic matter is removed by filtration though Celite under suction, the reaction mixture is washed with dilute hydrochloric acid (100 ml), water (200 ml×3) and saturated saline (200 ml×1) in this order until the mixture becomes neutral. The reaction mixture is dried over sodium sulfate anhydride, purified by silica gel column chromatography (hexane/ethyl acetate=3/1) and then vacuum-dried at 70° C. for 15 hours to give Intermediate 5B (5.4 g) in a yield of 53%.

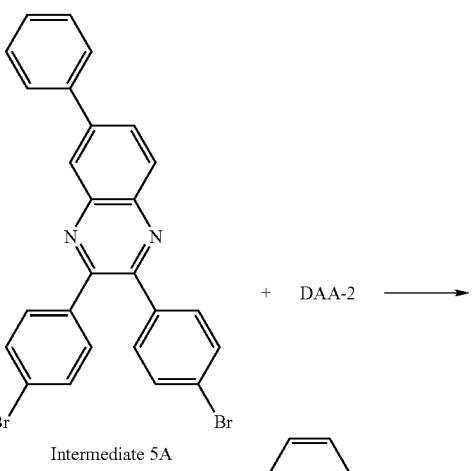
Intermediate 5A + DAA-2 ⟶

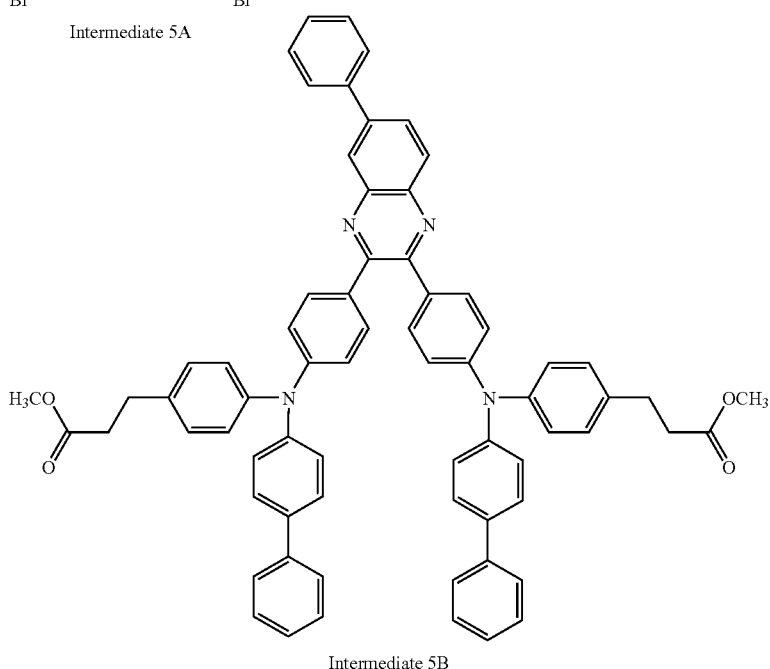
Intermediate 5B 1.0 g of Intermediate 5B is introduced into a 50-ml three-necked eggplant-shaped flask, and a tetrabutyl orthotitanate monomer (10 mg) in ethylene glycol (1.0 ml) is added thereto in a nitrogen atmosphere, and after degassing, the mixture is allowed to react at 200° C. for 5 hours. Thereafter, the mixture is heated to 210° C. at a reduced pressure of 45 Pa and allowed to react for 7 hours. The mixture is then cooled to room temperature (25° C.) and dissolved in 50 ml of monochlorobenzene under heating, and the insoluble matter is filtered out by filtration through a 0.5-μm PTFE filter under pressure, and the filtrate is added dropwise to 1000 ml of methanol under stirring, to re-precipitate a polymer. The polymer thus obtained is collected by filtration under suction, then washed with 500 ml of ethyl acetate/methanol, and dried to give 0.8 g of a polymer [exemplary compound (25)]. Analysis of the molecular weight of the exemplary compound (25) by gel-permeation chromatography (GPC) shows an MW of $7.3 \times 10^4$ (styrene-equivalent molecular weight) and an MW/Mn of 1.6, and the polymerization degree p as determined from the monomer molecular weight is 72.

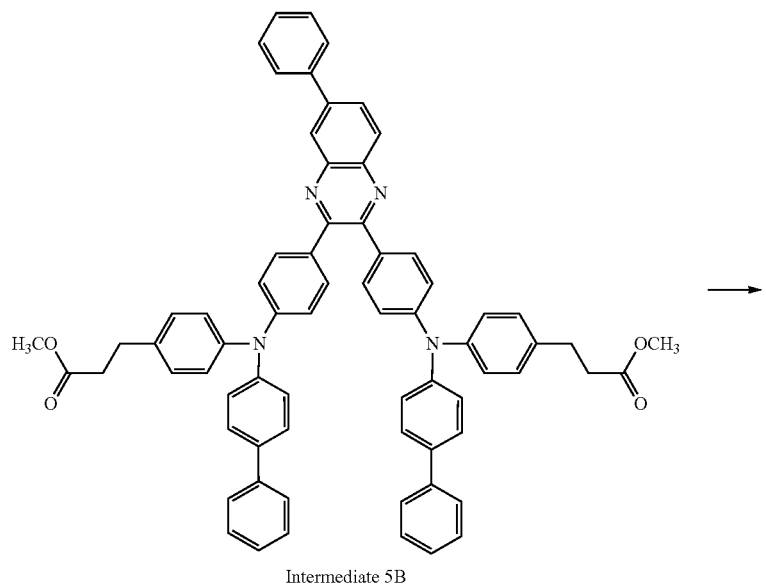

Intermediate 5B

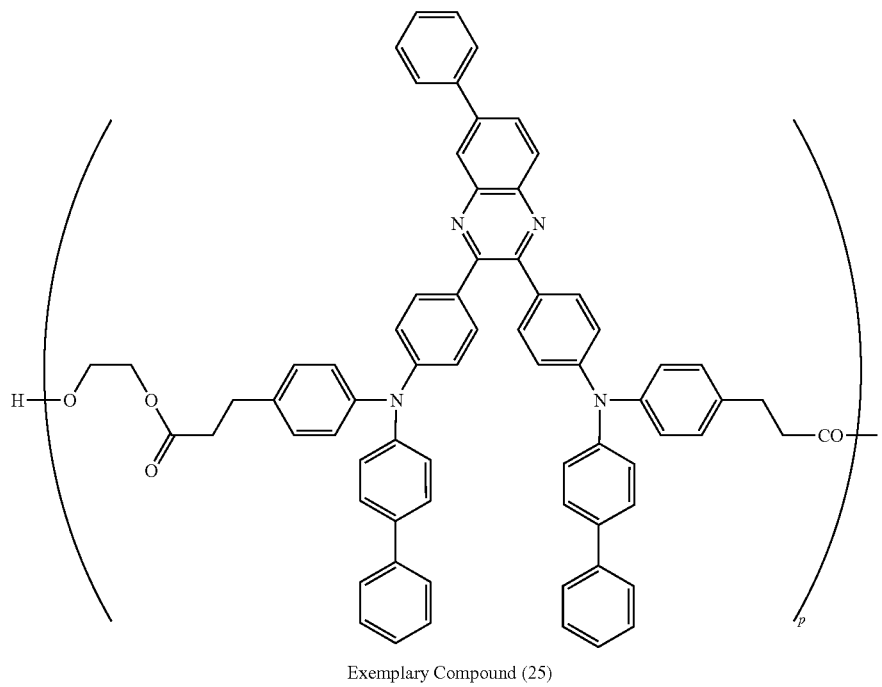

Exemplary Compound (25)

Preparation of an Element 1.5 wt % solution of a charge-transporting polyester [exemplary compound (25)] in dichloroethane solution is prepared and filtered through a 0.1-μm PTFE filter. On an ITO glass substrate etched and cleaned in the same manner as in Example 1 to form a strip-shaped ITO electrode of 2 mm in width, a hole-transporting layer of 0.05 μm in thickness is formed by an inkjet method using this solution. As a light emitting material, the exemplary compound (IV-14) is used to form a light-emitting layer of 0.050 μm in thickness by the inkjet method. After sufficient drying, Ca and Al are deposited thereon in thicknesses of 0.08 μm and 0.15 μm, respectively, to form a back electrode of 2 mm in width and 0.23 μm in total thickness such that the back electrode intersects with the ITO electrode. The effective area of the organic electroluminescence element formed is 0.04 cm$^2$.

Example 6

Synthesis Example 6

9,9-Dimethyl-2-acetamidofluorene (5.0 g), methyl 4-iodophenylpropionate (6.0 g), potassium carbonate (4.1 g) and copper sulfate pentahydrate (0.41 g) are introduced into a 100-ml three-necked flask equipped with a thermometer, a condenser and a magnetic stirrer, and then dissolved in o-dichlorobenzene (20 ml). The mixture is heated under stirring in a nitrogen atmosphere at 185° C. for 13 hours. After the reaction is finished, a solution of potassium hydroxide (1.5 g) in ethylene glycol (30 ml) is added thereto, the mixture is heated under reflux in a nitrogen atmosphere for 5 hours. After the reaction is finished, the reaction mixture is cooled to room temperature (25° C.), then poured into water (200 ml) and neutralized with hydrochloric acid, to give a crystalline precipitate. The crystal is collected by filtration, washed with water and transferred to a 1-L flask. Toluene (300 ml) is added thereto, the mixture is heated under reflux while water is removed by azeotropy, then a solution of conc. sulfuric acid (0.5 ml) in methanol (100 ml) is added, and the mixture is heated under reflux in a nitrogen stream for 3 hours. After the reaction is finished, the reaction mixture is poured into distilled water and extracted with toluene. The toluene layer is washed with distilled water, and after drying over sodium sulfate anhydride, the solvent is removed under reduced pressure, and recrystallization from an ethyl acetate/hexane mixture gives 5.0 g of DAA-3.

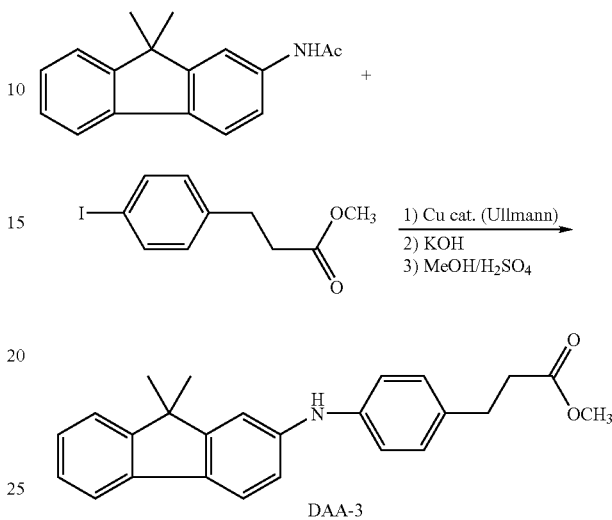

Then, DAA-3 (7.8 g), Intermediate 4A (4.5 g), palladium (II) acetate (110 mg), and rubidium carbonate (14 g) are introduced into a 300-ml three-necked flask equipped with a thermometer, a condenser and a magnetic stirrer, and then dissolved in 200 ml of xylene. Tri(tertiary-butyl)phosphine (800 mg) is quickly added thereto, and the mixture is heated under reflux for 12 hours under stirring with the magnetic stirrer in a nitrogen atmosphere. After the disappearance of the spot of Intermediate 4A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (100 ml), water (200 ml×3) and saturated saline (200 ml×1) in this order until the mixture becomes neutral. The reaction mixture is dried over sodium sulfate anhydride, purified by silica gel column chromatography (hexane/ethyl acetate=3/1) and then vacuum-dried at 70° C. for 15 hours to give Intermediate 6A (6.2 g) in a yield of 60%.

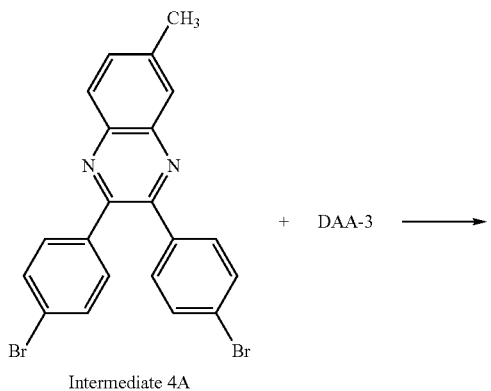

Intermediate 4A

-continued

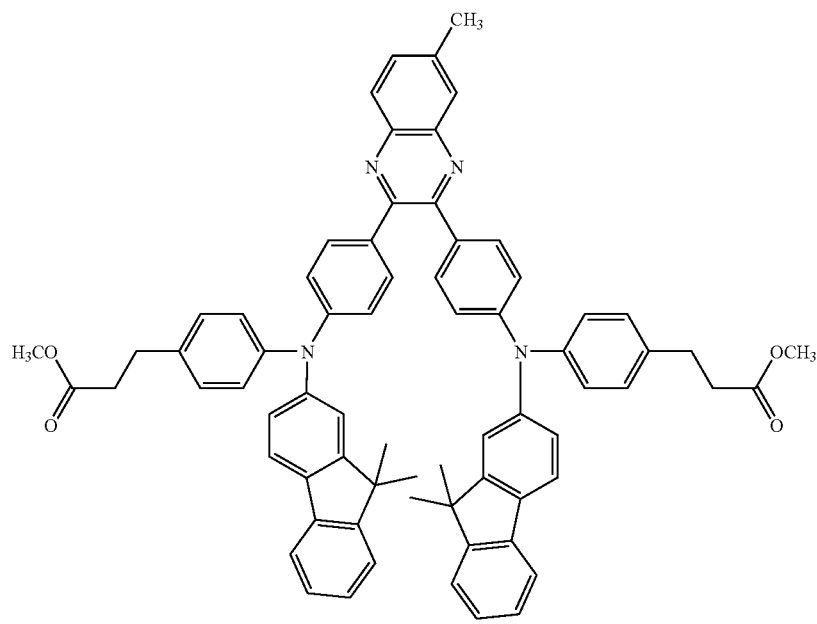

Intermediate 6A 1.0 g of Intermediate 6A is introduced into a 50-ml three-necked eggplant-shaped flask, and a tetrabutyl orthotitanate monomer (10 mg) in hexylene glycol (10 ml) is added thereto in a nitrogen atmosphere, and after degassing, the mixture is allowed to react at 200° C. for 5 hours. Thereafter, the mixture is heated to 200° C. at a reduced pressure of 42 Pa and allowed to react for 6 hours. The mixture is then cooled to room temperature (25° C.) and dissolved in 50 ml of monochlorobenzene under heating, and the insoluble matter is filtered out by filtration through a 0.5-μm PTFE filter under pressure, and the filtrate is added dropwise to 1000 ml of ethyl acetate/methanol under stirring, to re-precipitate a polymer. The polymer thus obtained is collected by filtration under suction, then washed with 500 ml of ethyl acetate/methanol, and dried to give 0.8 g of a polymer [exemplary compound (64)]. Analysis of the molecular weight of the exemplary compound (64) by gel-permeation chromatography (GPC) shows an MW of $8.6 \times 10^4$ (styrene-equivalent molecular weight) and an MW/Mn of 1.4, and the polymerization degree p as determined from the monomer molecular weight is 82.

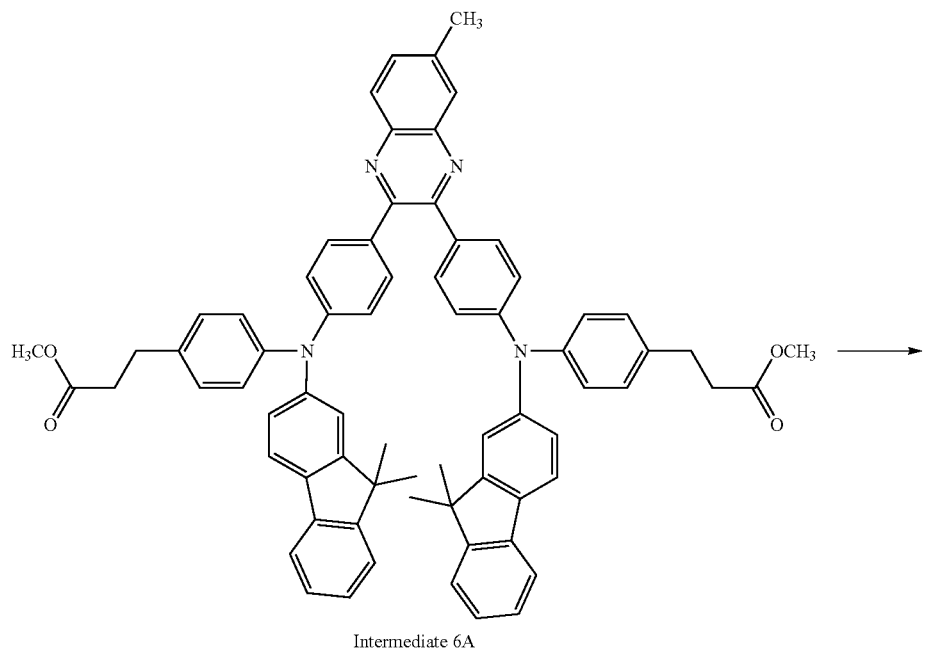

Intermediate 6A

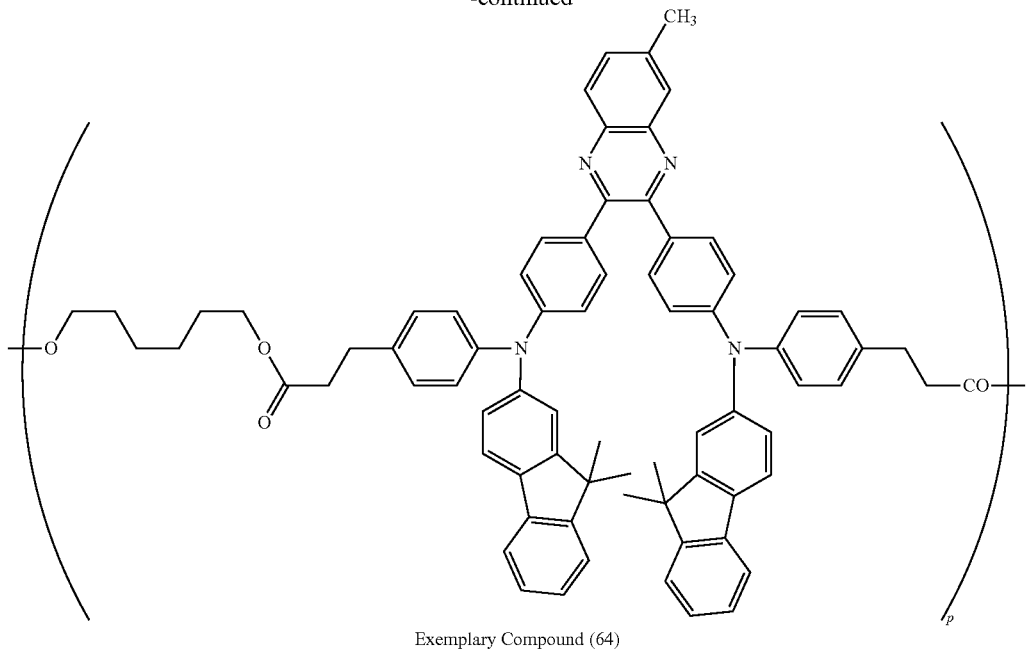

Exemplary Compound (64)

Preparation of an Element

On an ITO glass substrate etched and cleaned in the same manner as in Example 1, a non-conjugated polymer [exemplary compound (64)] is formed as a hole-transporting, light-emitting layer with a thickness of 0.050 μm in a similar manner to Example 1. The exemplary compound (IV-9) is formed as an electron-transporting layer having a thickness of 0.030 μm. Subsequently, in a width of 2 mm, LiF and Al are deposited thereon in thicknesses of 0.005 μm and 0.15 μm, respectively, to form a back electrode such that the back electrode intersects with the ITO electrode. The effective area of the organic electroluminescence element formed is 0.04 $cm^2$.

Example 7

Synthesis Example 7

4,5-Difluoro-1,2-phenylenediamine (2.9 g) and 4.4'-dibromobenzil (3.7 g) are introduced into a 500-ml three-necked flask equipped with a thermometer, a condenser and a magnetic stirrer, and then dissolved in 200 ml of isopropyl ether. The mixture is heated under reflux for 1 hour under stirring with the magnetic stirrer. After the disappearance of the spot of 4,5-difluoro-1,2-phenylenediamine is confirmed by TLC (hexane/ethyl acetate=3/1), the reaction mixture is cooled to room temperature (25° C.). Crystals precipitated during the reaction, and are collected by filtration under suction. The crystals are washed with 50 ml of methanol and then vacuum-dried at 70° C. for 15 hours to give a quinoxaline dihalogen derivative [Intermediate 7A] (4.3 g).

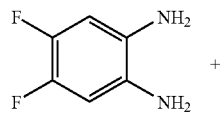

+

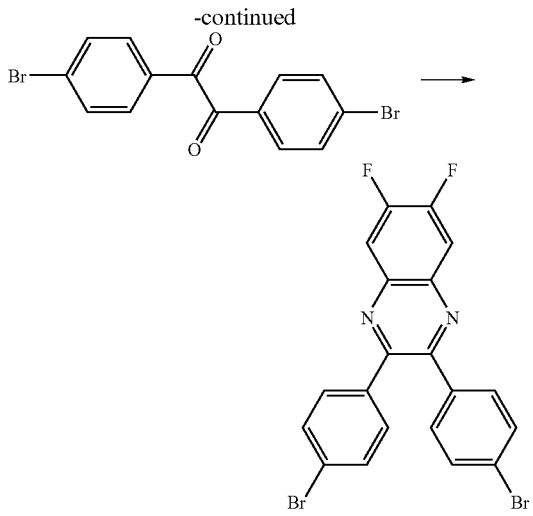

Intermediate 7A 2-(4-acetamidophenyl)-5-p-tert-butylphenyl(1,3,4)oxa-diazole (3.4 g), methyl 4-iodophenylpropionate (3.0 g), potassium carbonate (2.0 g) and copper sulfate pentahydrate (0.20 g) are introduced into a 100-ml three-necked flask equipped with a thermometer, a condenser and a magnetic stirrer, and then dissolved in o-dichlorobenzene (20 ml). The mixture is heated under stirring in a nitrogen atmosphere at 185° C. for 13 hours. After the reaction is finished, a solution of potassium hydroxide (0.76 g) in ethylene glycol (30 ml) is added thereto, the mixture is heated under reflux in a nitrogen atmosphere for 5 hours. After the reaction is finished, the reaction mixture is cooled to room temperature (25° C.), then poured into water (200 ml) and neutralized with hydrochloric acid, to give a crystalline precipitate. The crystal is collected by filtration, washed with water and transferred to a 500-mL flask. Toluene (200 ml) is added thereto, the mixture is heated under reflux while water is removed by azeotropy, then a solution of conc. sulfuric acid (0.5 ml) in methanol (100 ml) is added, and the mixture is heated under reflux in a nitrogen stream for 3 hours. After the reaction is finished, the reaction mixture is poured into distilled water and extracted with toluene. The toluene layer is washed with distilled water, and after drying over sodium sulfate anhydride, the solvent is removed under reduced pressure, and recrystallization from an ethyl acetate/hexane mixture gives 3.2 g of DAA-4.

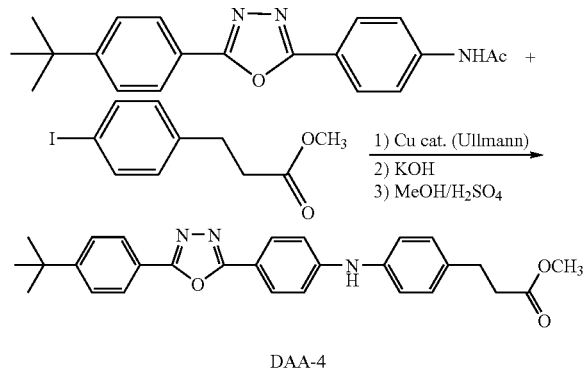

Then, DAA-4 (2.3 g), Intermediate 7A (1.0 g), palladium (II) acetate (22 mg), and rubidium carbonate (2.9 g) are introduced into a 200-ml three-necked flask equipped with a thermometer, a condenser and a magnetic stirrer, and then dissolved in 50 ml of xylene. Tri(tertiary-butyl)phosphine (170 mg) is quickly added thereto, and the mixture is heated under reflux for 10 hours under stirring with the magnetic stirrer in a nitrogen atmosphere. After the disappearance of the spot of Intermediate 7A is confirmed by TLC (hexane/ethyl acetate=3/1), the reaction mixture is cooled to room temperature (25° C.). After inorganic matter is removed by filtration through Celite under suction, the reaction mixture is washed with dilute hydrochloric acid (50 ml), water (50 ml×3) and saturated saline (50 ml×1) in this order until the mixture becomes neutral. The reaction mixture is dried over sodium sulfate anhydride, purified by silica gel column chromatography (hexane/ethyl acetate=3/1) and then vacuum-dried at 70° C. for 15 hours to give Intermediate 7B (1.5 g) in a yield of 59%.

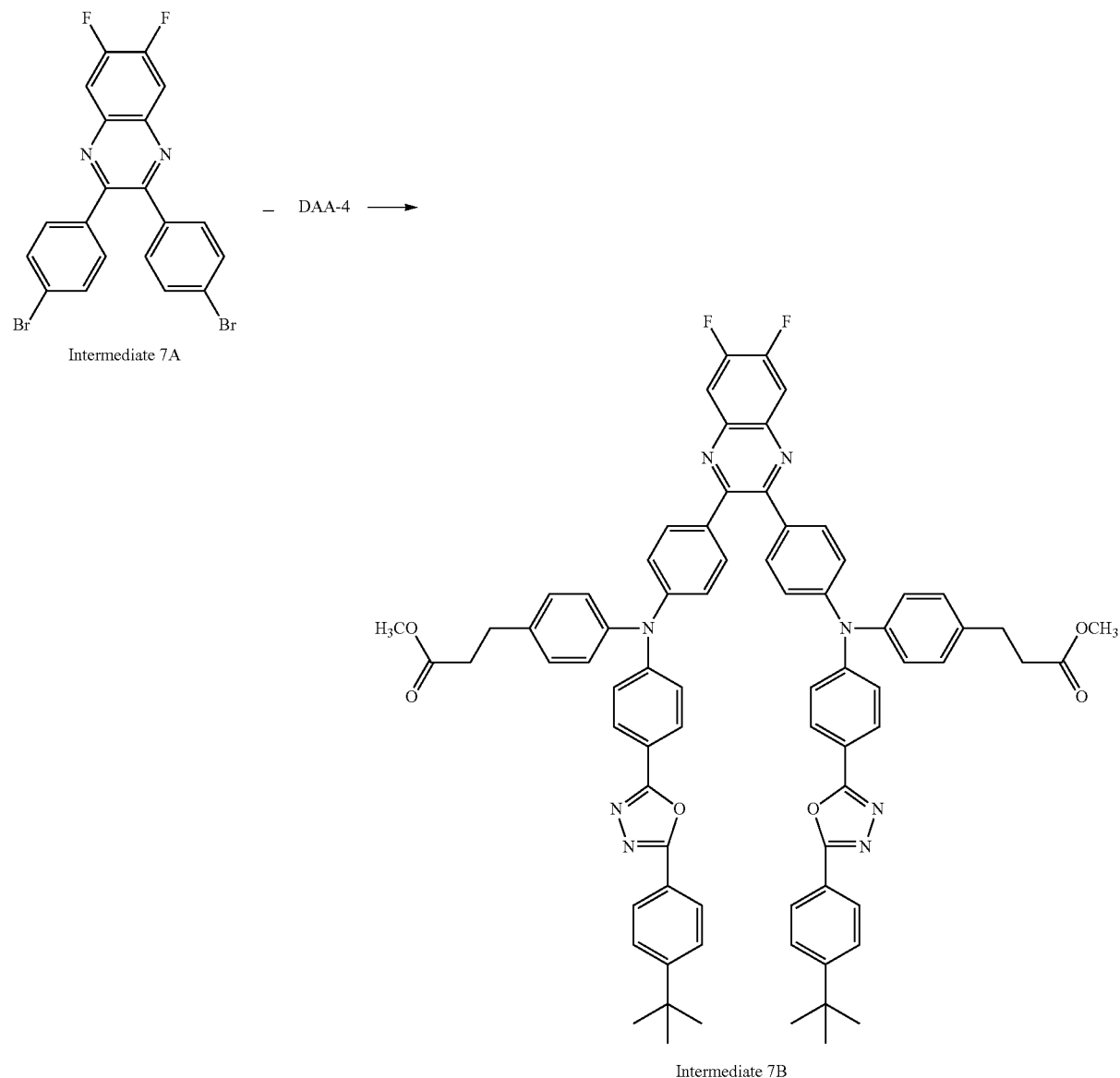

1.0 g of Intermediate 7B is introduced into a 50-ml three-necked eggplant-shaped flask, and a tetrabutyl orthotitanate monomer (10 mg) in ethylene glycol (10 ml) is added thereto in a nitrogen atmosphere, and after degassing, the mixture is allowed to react at 200° C. for 5 hours. Thereafter, the mixture is heated to 180° C. at a reduced pressure of 70 Pa and allowed to react for 6 hours. The mixture is then cooled to room temperature (25° C.) and dissolved in 50 ml of monochlorobenzene under heating, and the insoluble matter is filtered out by filtration through a 0.5-μm PTFE filter under pressure, and the filtrate is added dropwise to 1000 ml of ethyl acetate/methanol under stirring, to re-precipitate a polymer. The polymer thus obtained is collected by filtration under suction, then washed with 500 ml of ethyl acetate/methanol, and dried to give 0.9 g of a polymer [exemplary compound (83)]. Analysis of the molecular weight of the exemplary compound (83) by gel-permeation chromatography (GPC) shows an MW of $9.9 \times 10^4$ (styrene-equivalent molecular weight) and an MW/Mn of 2.2, and the polymerization degree p as determined from the monomer molecular weight is 80.

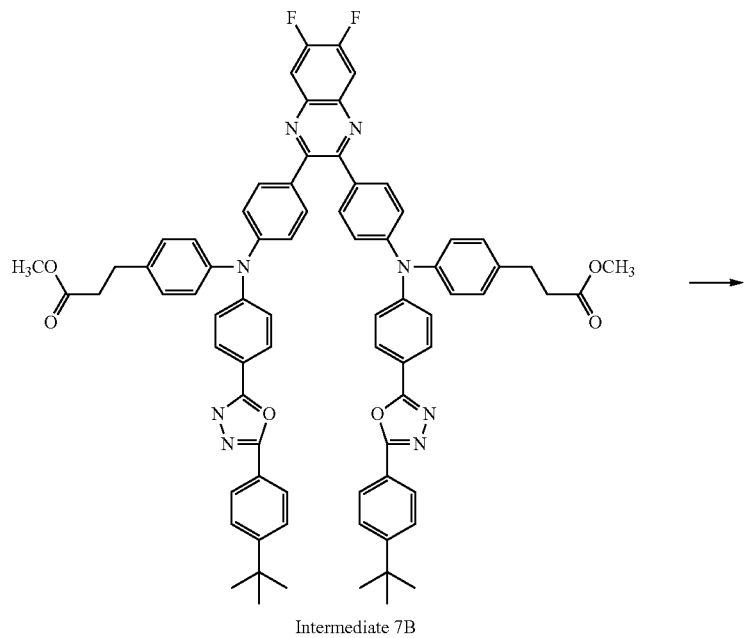

Intermediate 7B

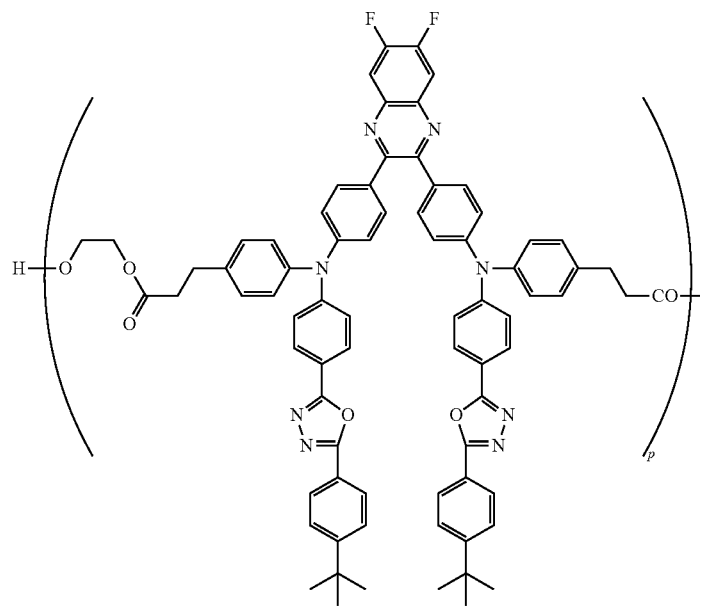

Exemplary Compound (83)

Preparation of an Element 1.5 weight % solution of a charge-transporting polyester [exemplary compound (83)] in dichloroethane is prepared and filtered through a 0.1-μm PTFE filter. On an ITO glass substrate etched and cleaned in the same manner as in Example 1 to form a strip-shaped ITO electrode of 2 mm in width, a hole-transporting, light-emitting, electron-transporting layer of 0.05 μm in thickness is formed by an inkjet method using the solution, in a similar manner to Example 1. Subsequently, in a width of 2 mm, LiF and Al are deposited thereon in thicknesses of 0.005 μm and 0.15 μm, respectively, to form a back electrode such that the back electrode intersects with the ITO electrode. The effective area of the organic electroluminescence element formed is 0.04 cm$^2$.

Comparative Example 1

An element is prepared in the same manner as in Example 1 except that the compound represented by the structural formula (VI) below is used in place of the exemplary compound (1) used in Example 1.

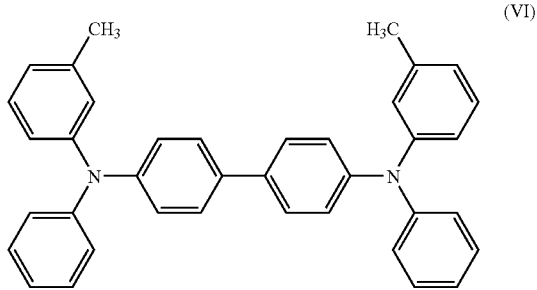

(VI)

Comparative Example 2

2 parts by weight of polyvinyl carbazole (PVK) as a charge transporting polymer, 0.1 part by weight of the exemplary compound (V-1) as a light emitting material and 1 part by weight of the compound (IV-9) as an electron transporting material are mixed, and a 10% by weight solution of the mixture in dichloroethane is prepared. Then the solution is filtered through a 0.1-μm PTFE filter. A glass substrate having a strip-shaped ITO electrode of 2 mm in width formed by etching is coated with this solution by dipping to form a hole-transporting layer of 0.15 μm in thickness. After sufficient drying, an Mg—Ag alloy is co-deposited thereon to form a back electrode having a width of 2 mm and a thickness of 0.15 μm such that the back electrode intersects with the ITO electrode. The effective area of the organic electroluminescence element formed is 0.04 cm$^2$.

Evaluation

Each of the organic EL elements prepared as described above is sealed via an adhesive with glass in dry nitrogen and then a measurement is conducted with the ITO electrode being positive and the Mg—Ag back electrode being negative.

Light emitting properties are compared in terms of driving current density wherein the initial brightness is 400 cd/m$^2$ in a direct current driving system (DC driving). The emission lifetime is evaluated in terms of relative driving time assuming that the driving time elapsed until the brightness (initial brightness $L_0$: 400 cd/m$^2$) of the element of Comparative Example 1 at room temperature (25° C.) becomes half the initial brightness (that is, the brightness L/initial brightness $L_0$ ratio becomes 0.5) is 1.0, as well as in terms of voltage increase (=voltage/initial driving voltage) at the time the brightness of the element becomes half the initial brightness (that is, the brightness L/initial brightness $L_0$ ratio becomes 0.5). The results are shown in Table 1.

ADC voltage of 5 V is applied to each of the obtained organic electroluminescence elements with the ITO electrode serving as a positive electrode and the back electrode serving as a negative electrode under vacuum (1.33×10$^{-1}$ Pa), and its emission is measured to evaluate the maximum brightness and emission color. The results are shown in Table 1.

TABLE 1

| | Maximum brightness (cd/m$^2$) | Emission color | Driving current density (mA/cm$^2$) | Voltage increase (L/L$_0$ = 0.5) | Relative time (L/L$_0$ = 0.5) |
|---|---|---|---|---|---|
| Example 1 | 18500 | yellow | 14.8 | 1.10 | 1.47 |
| Example 2 | 16300 | yellow | 15.5 | 1.09 | 1.33 |
| Example 3 | 20500 | yellow | 15.1 | 1.07 | 1.70 |
| Example 4 | 16500 | yellow | 16.3 | 1.11 | 1.62 |
| Example 5 | 19300 | yellow | 16.1 | 1.08 | 1.55 |
| Example 6 | 20400 | yellow | 16.5 | 1.12 | 1.30 |
| Example 7 | 21500 | yellow | 17.3 | 1.20 | 1.45 |
| Comparative example 1 | 11000 | green | 14.6 | 1.32 | 1.00 |
| Comparative example 2 | 8750 | green | 15.7 | 1.25 | 1.08 |

What is claimed is:

1. An organic electroluminescence element comprising a pair of electrodes composed of an anode and a cathode, at Least one of which is transparent or semitransparent, and one or more organic compound layers disposed between the pair of electrodes, at least one of the organic compound layers comprising at least one charge-transporting polyester consisting of repeating units containing, as a partial structure, at least one structure represented by the following formula (I-1):

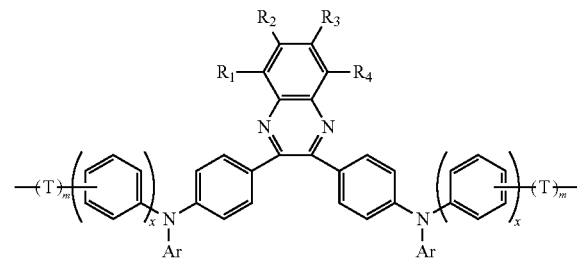

(I-1)

in the formula (I-1), $R_1$, $R_2$, $R_3$ and $R_4$ each independently representing a hydrogen atom, a substituted or unsubstituted monovalent hydrocarbon group having 1 to 10 carbon atoms, a substituted or unsubstituted monovalent phenyl group, a halogen atom, a substituted or unsubstituted monovalent polynuclear aromatic hydrocarbon group having 2 to 10 aromatic rings, a substituted or unsubstituted monovalent condensed aromatic hydrocarbon group having 2 to 10 aromatic rings, or a substituted or unsubstituted monovalent aromatic heterocyclic group; Ar representing a substituted or unsubstituted monovalent phenyl group, a substituted or unsubstituted monovalent polynuclear aromatic hydrocarbon group having 2 to 10 aromatic rings, a substituted or unsubstituted monovalent condensed polycyclic aromatic hydrocarbon group having 2 to 10 aromatic rings, a substituted or unsubstituted monovalent aromatic heterocyclic group, or a monovalent aromatic group containing at least one aromatic heterocycle; T representing a divalent linear hydrocarbon group having 1 to 10 carbon atoms or a divalent branched hydrocarbon group having 2 to 10 carbon atoms; and x representing an integer of 3 and m representing an integer of 0 to 3 or x representing an integer of 1 to 3 and m representing an integer of 2 to 3.

2. The organic electroluminescence element according to claim 1, wherein the one or more organic compound layers comprise at least one layer selected from a light-emitting layer, an electron-transporting layer and an electron injection layer, and the at least one layer selected from the light-emitting layer, the electron-transporting layer and the electron injection layer comprises at least one charge-transporting polyester consisting of repeating units containing, as a partial structure, at least one structure represented by the formula (I-1).

3. The organic electroluminescence element according to claim 1, wherein the one or more organic compound layers comprise at least one layer selected from a light-emitting layer, a hole-transporting layer and a hole injection layer, and the at least one layer selected from the light-emitting layer, the hole-transporting layer and the hole injection layer comprises at least one charge-transporting polyester consisting of repeating units containing, as a partial structure, at least one structure represented by the formula (I-1).

4. The organic electroluminescence element according to claim 3, wherein the at least one layer is a hole-transporting layer comprising the at least one charge-transporting polyester.

5. The organic electroluminescence element according to claim 1, wherein the one or more organic compound layers comprise at least one layer selected from a light-emitting layer, a hole-transporting layer and a hole injection layer and at least one layer selected from an electron-transporting layer and an electron injection layer, and at least one layer selected from the light-emitting layer, the hole-transporting layer, the hole injection layer, the electron-transporting layer and the electron injection layer comprises at least one charge-transporting polyester consisting of repeating units containing, as a partial structure, at least one structure represented by the formula (I-1).

6. The organic electroluminescence element according to claim 1, wherein the one or more organic compound layers are composed only of a light-emitting layer having a charge transporting function, and the light-emitting layer having a charge transporting function comprises at least one charge-transporting polyester consisting of repeating units containing, as a partial structure, at least one structure represented by the formula (I-1).

7. The organic electroluminescence element according to claim 1, wherein the charge-transporting polyester consisting of repeating units containing, as a partial structure, at least one structure represented by the formula (I-1) is a charge-transporting polyester represented by the following formulae (II-1) or (II-2):

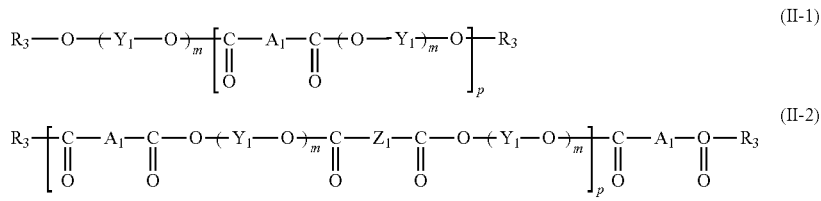

wherein, in the formulae (II-1) and (II-2), $A_1$ represents at least one structure represented by the formula (I-1); $Y_1$ represents a divalent alcohol residue; $Z_1$ represents a divalent carboxylic acid residue; m represents an integer of 1 to 5; p represents an integer of 5 to 5000; and each $R_3$ independently represents a hydrogen atom, —O—$(Y_1\text{-}O)_m$—H, or —O—$(Y_1\text{—}O)_m$—CO—$Z_1$—CO—OR' wherein R' represents a hydrogen atom, an alkyl group, a substituted or unsubstituted aryl group, or a substituted or unsubstituted aralkyl group, and $Y_1$, $Z_1$ and m have the same definitions as above.

8. The organic electroluminescence device according to claim 1, wherein x in the formula (I-1) is 1.

9. A display device comprising:
an organic electroluminescence element arranged in at least one of a matrix shape and a segment shape, the element comprising a pair of electrodes composed of an anode and a cathode, at least one of which is transparent or semitransparent, and one or more organic compound layers disposed between the pair of electrodes, at least one of the organic compound layers comprising at least one charge-transporting polyester consisting of repeating units containing, as a partial structure, at least one structure represented by the following formula (I-1), and
a drive unit that drives the organic electroluminescence elements arranged in a matrix and/or segment shape:

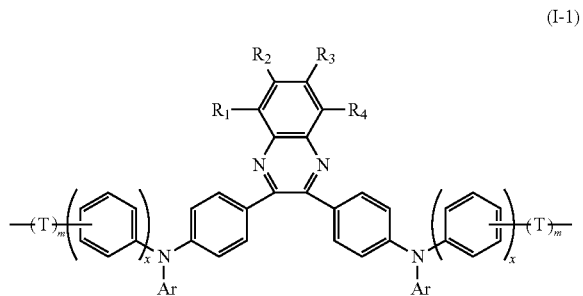

in the formula (I-1), $R_1$, $R_2$, $R_3$ and $R_4$ each independently representing a hydrogen atom, a substituted or unsubstituted monovalent hydrocarbon group having 1 to 10 carbon atoms, a substituted or unsubstituted monovalent phenyl group, a halogen atom, a substituted or unsubstituted monovalent polynuclear aromatic hydrocarbon group having 2 to 10 aromatic rings, a substituted or unsubstituted monovalent condensed aromatic hydrocarbon group having 2 to 10 aromatic rings, or a substituted or unsubstituted monovalent aromatic heterocyclic group; Ar representing a substituted or unsubstituted monovalent phenyl group, a substituted or unsubstituted monovalent polynuclear aromatic hydrocarbon group having 2 to 10 aromatic rings, a substituted or unsubstituted monovalent condensed polycyclic aromatic hydrocarbon group having 2 to 10 aromatic rings, a substituted or unsubstituted monovalent aromatic heterocyclic group, or a monovalent aromatic group containing at least one aromatic heterocycle; T representing a divalent linear hydrocarbon group having 1 to 10 carbon atoms or a divalent branched hydrocarbon group having 2 to 10 carbon atoms; and x representing an integer of 3 and m representing an integer of 0 to 3 or x representing an integer of 1 to 3 and m representing an integer of 2 to 3.

10. The display device according to claim 9, wherein x in the formula (I-1) is 1.

* * * * *